United States Patent
Someya et al.

(10) Patent No.: US 12,248,119 B2
(45) Date of Patent: Mar. 11, 2025

(54) COMPOUND, RESIN PRECURSOR, CURED OBJECT, OPTICAL ELEMENT, OPTICAL SYSTEM, INTERCHANGEABLE CAMERA LENS, OPTICAL DEVICE, CEMENTED LENS, AND METHOD FOR MANUFACTURING CEMENTED LENS

(71) Applicant: NIKON CORPORATION, Tokyo (JP)

(72) Inventors: Yoshihiro Someya, Yamato (JP); Masayuki Shijo, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 589 days.

(21) Appl. No.: 17/565,881

(22) Filed: Dec. 30, 2021

(65) Prior Publication Data

US 2022/0120937 A1  Apr. 21, 2022

Related U.S. Application Data

(63) Continuation of application No. PCT/JP2019/026021, filed on Jul. 1, 2019.

(51) Int. Cl.
| | |
|---|---|
| *G02B 1/04* | (2006.01) |
| *C07D 487/00* | (2006.01) |
| *C08F 18/14* | (2006.01) |
| *G02B 7/02* | (2021.01) |

(52) U.S. Cl.
CPC .......... *G02B 1/041* (2013.01); *C07D 487/00* (2013.01); *C08F 18/14* (2013.01); *G02B 7/021* (2013.01); *G02B 7/025* (2013.01)

(58) Field of Classification Search
CPC ........ G02B 1/00–1/18; C07D 249/18–249/20; C07D 487/00–487/22
See application file for complete search history.

(56) References Cited

U.S. PATENT DOCUMENTS

| | | | | |
|---|---|---|---|---|
| 4,716,234 A | * | 12/1987 | Dunks | C08F 20/36 548/259 |
| 9,005,700 B2 | * | 4/2015 | Bothe | B05D 5/06 427/164 |
| 2013/0095235 A1 | | 4/2013 | Bothe et al. | |
| 2017/0217937 A1 | * | 8/2017 | Kawai | C08K 5/37 |

OTHER PUBLICATIONS

International Search Report, dated Sep. 17, 2019, in corresponding International Application No. PCT/JP2019/026021 (4 pp.).

* cited by examiner

*Primary Examiner* — Prashant J Khatri

(57) ABSTRACT

A compound represented by Formula (1) given below. (In the formula, $R^1$ represents a hydrogen atom of a methyl group, and X represents a $C_{2\ to\ 6}$ alkylene group, a $C_{4\ to\ 6}$ alkylene group containing an oxygen atom and/or a sulfur atom, or a $C_{3\ to\ 6}$ alkylene group in which at least one hydrogen is replaced with an acryloxy group or a methacryloxy group.)

23 Claims, 6 Drawing Sheets

COMPOUND, RESIN PRECURSOR, CURED OBJECT, OPTICAL ELEMENT, OPTICAL SYSTEM, INTERCHANGEABLE CAMERA LENS, OPTICAL DEVICE, CEMENTED LENS, AND METHOD FOR MANUFACTURING CEMENTED LENS

CROSS REFERENCE TO RELATED APPLICATIONS

This application is a continuation of International Patent Application No. PCT/JP2019/026021 filed on Jul. 1, 2019, the contents of which are incorporated herein by reference.

TECHNICAL FIELD

The present invention relates to a compound, a resin precursor, a cured object, an optical element, an optical system, an interchangeable camera lens, an optical device, a cemented lens, and a method for manufacturing cemented lens.

BACKGROUND ART

For example, JP 2016-095542 A (PTL 1) discloses a cemented lens obtained by adhering an object-side lens having negative power and an image-side lens having positive power by using a resin adhesive layer. For satisfactory correction of chromatic aberrations, a material having a large $\theta_{g,F}$ value is demanded for the resin adhesive layer used in such cemented lens.

PTL 1: JP 2016-095542 A

SUMMARY

A first aspect according to the present invention is a compound represented by Formula (1) given below.

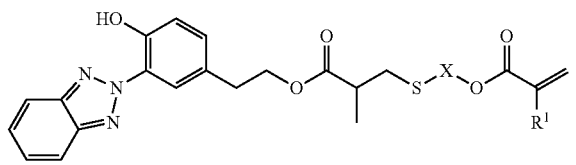

(1)

(In the formula, $R^1$ represents a hydrogen atom or a methyl group, and X represents a $C_{2\ to\ 6}$ alkylene group, a $C_{4\ to\ 6}$ alkylene group containing an oxygen atom and/or a sulfur atom, or a $C_{3\ to\ 6}$ alkylene group in which at least one hydrogen is replaced with an acryloxy group or a methacryloxy group.)

A second aspect according to the present invention is a resin precursor containing the compound described above and a curable composition.

A third aspect according to the present invention is a cured object obtained by curing the resin precursor described above.

A fourth aspect according to the present invention is an optical element using the cured object described above.

A fifth aspect according to the present invention is an optical system including the optical element described above.

A sixth aspect according to the present invention is an interchangeable camera lens including the optical system described above.

A seventh aspect according to the present invention is an optical device including the optical system described above.

An eighth aspect according to the present invention is a cemented lens including a first lens element and a second lens element joined with each other through intermediation of the cured object described above.

A ninth aspect according to the present invention is a method of manufacturing a cemented lens including a contacting step of contacting a first lens element and a second lens element with each other through intermediation of the resin precursor described above, and a joining step of curing the resin precursor described above to join the first lens element and the second lens element with each other.

DETAILED DESCRIPTION

Figure 1:
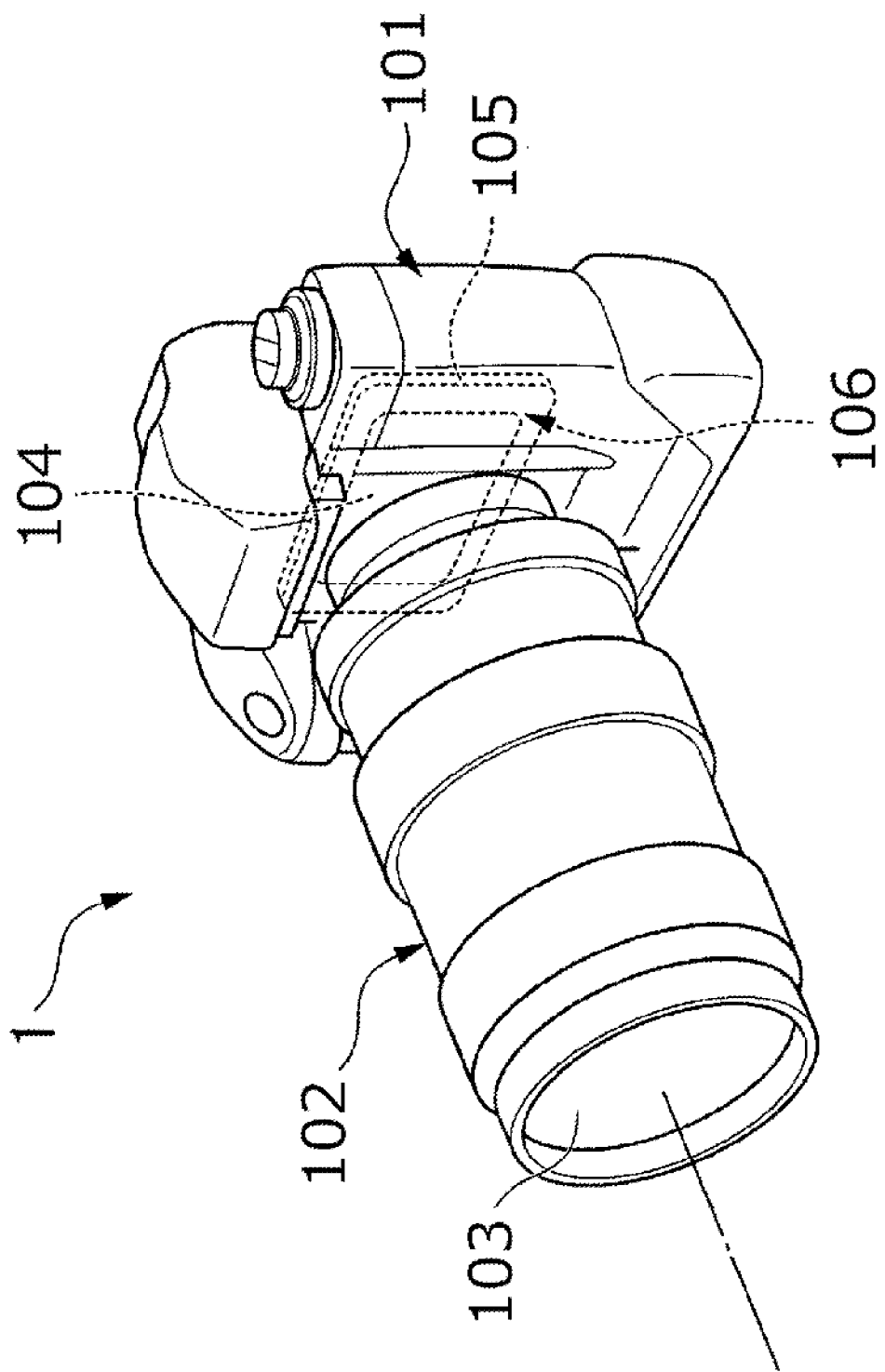
FIG. 1 is a perspective view of one example of an optical device according to the present embodiment as an imaging device.

An embodiment of the present invention (hereinafter, simply referred to as the "present embodiment") is described in detail. The present embodiment described below is an example for describing the present invention, and is not intended to limit the present invention to the contents described below. Note that, in the drawings, a positional relationship such as up, down, right, left, and the like is based on a positional relationship illustrated in the drawings, unless otherwise noted. Further, a dimensional ratio in the drawings is not intended to limit the dimensional ratio in the drawings. An acrylate and a methacrylate are collectively referred to as a "(meth)acrylate" in some cases.

A compound according to the present embodiment is a compound represented by Formula (1) given below.

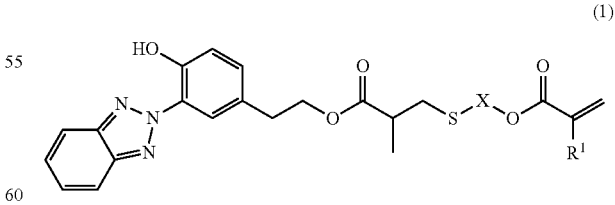

(1)

(In the formula, $R^1$ represents a hydrogen atom or a methyl group, and X represents a $C_{2\ to\ 6}$ alkylene group, a $C_{4\ to\ 6}$ alkylene group containing an oxygen atom and/or a sulfur atom, or a $C_{3\ to\ 6}$ alkylene group in which at least one hydrogen is replaced with an acryloxy group or a methacryloxy group.)

The compound represented by Formula (1) (hereinafter, referred to as the "compound (1)" in some cases) is a novel compound having a benzotriazole skeleton. The compound (1) can be used suitable as one composition of a resin precursor being a material for an optical element or the like. Further, when such compound is used, an optical element having an excellent $\theta_{g,F}$ value can be obtained. Particularly, when such compound is used as a material for a multi-layer optical element (cemented lens) obtained by combining a concave lens and a convex lens with each other, the optical element can exert an excellent optical characteristic while having a thin shape, and an excellent chromatic aberration correction effect can be provided. Note that a $\theta_{g,F}$ value is a value indicated by $(n_g-n_F)/(n_F-n_C)$ with respect to a C-line (having a wavelength of 656.3 nm), an F-line (having a wavelength of 486.1 nm), and a g-line (having a wavelength of 435.8 nm) when refractive indexes are represented by $n_C$, $n_F$, and $n_g$, respectively.

<Compound (1)>

A structure of the compound (1) is described below.

$R^1$ represents a hydrogen atom or a methyl group.

X represents a $C_{2\ to\ 6}$ alkylene group, a $C_{4\ to\ 6}$ alkylene group containing an oxygen atom and/or a sulfur atom, or a $C_{3\ to\ 6}$ alkylene group in which at least one hydrogen is replaced with an (meth)acryloxy group.

Specific examples of the $C_{2\ to\ 6}$ alkylene group include an ehylene group, an n-propylene group, an n-butylene group, a 2-methylpropylene group, 1-2-dimethylethylene group, an n-pentylene group, a 1,3-dimethylepropylene group, a 2,2-dimethylpropylene group, an n-hexylene group, a 3-methylpentylene group, a 2,3-dimethylbutylene group, a 1, 2, 3-trimethylpropylene group, and a 1,1,2,2-tetramethylethylene group. Among those, an ethylene group, an n-propylene group, and a 1,2-dimethylethylene group are preferred, from a perspective of stability and the like at the time of preparing the resin precursor or the like.

The uppermost number of carbon atoms of the $C_{2\ to\ 6}$ alkylene group is preferably 5, more preferably, 4. An alkylene group may be linear or branched.

Specific examples of the $C_{4\ to\ 6}$ alkylene group containing an oxygen atom and/or a sulfur atom include a 3-oxapentylene group, a 3-thiapentylene group, a 3,6-dioxaheptylene group, a 3,6-dithiaheptylene group, and a 3-oxa-6-thiaheptylene. Among those, a 3-oxapentylene group and a 3,6-dioxaheptylene group are preferred, from a perspective of stability and the like at the time of preparing the resin precursor or the like. The number of carbon atoms of the $C_{4\ to\ 6}$ alkylene group is preferably 4.

Specific examples of the $C_{3\ to\ 6}$ alkylene group in which at least one hydrogen is replaced with an (meth)acryloxy group include a 2-(meth)acryloxypropylene group, a 3-(meth)acryloxybutylene group, a 3-(meth)acryloxypentylene group, and a 4-(meth)acryloxyhexylene group. Among those, a 2-(meth)acryloxypropylene group is preferred, from a perspective of stability and the like at the time of preparing the resin precursor or the like. The number of carbon atoms of the $C_{3\ to\ 6}$ alkylene group is preferably 3.

<Resin Precursor>

According to the present embodiment, a resin precursor containing the compound (1) and a curable composition can be obtained. The resin precursor can be used suitably as a resin precursor for an optical material. When used as an optical material, it is desired that the resin precursor is stable in a liquid state under an ordinary temperature and pressure. From this perspective, the resin precursor according to the present embodiment is preferably in a liquid state under an ordinary temperature and pressure. Further, when a component described later is used together with the compound (1), deposition of an insoluble component can be effectively prevented, and preparation for a stable liquid-state composition can be facilitated.

The curable composition may be photocurable or thermocurable, and is preferably a photocurable composition. For example, when a large amount of a (meth)acrylate-based compound is contained, a photocurable composition is preferred.

The curable composition is not specifically limited. However, for example, one or more compound selected from a group consisting of a compound represented by Formula (2) given below, a fluorine-containing (meth)acrylate compound, a (meth)acrylate compound having a fluorene structure, and a di(meth)acrylate compound may be used. When such component is used together with the compound (1), deposition of an insoluble component can be effectively prevented, and preparation for a stable liquid composition can be facilitated. As a result, generation of deposits can be prevented during storage, and an operation of removing deposits is not required before using the composition. A uniformly cured object having a low refractive index and high dispersion can be obtained.

(2)

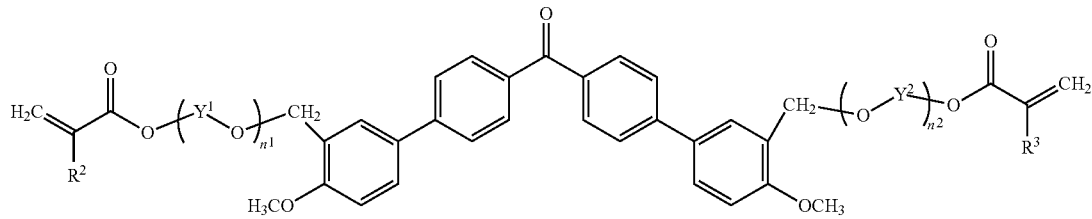

(In the formula, $R^2$ and $R^3$ independently represent a hydrogen atom or a methyl group, $Y^1$ and $Y^2$ independently represent a $C_{1\ to\ 9}$ alkylene group, and $n^1$ and $n^2$ independently represent an integer from 0 to 3.)

The compound represented by Formula (2) (hereinafter, referred to as the "compound (2)" in some cases) is described below.

$Y^1$ and $Y^2$ independently represent a $C_{1\ to\ 9}$ alkylene group. An alkylene group may be linear or branched. From a perspective of prevention of deposition of an insoluble component, stability, and the like at the time of preparing the resin precursor or the like, the uppermost number of carbon atoms is preferably 5, more preferably, 4. Further, the lowermost number of carbon atoms is preferably 2.

Specific examples of $Y^1$ and $Y^2$ include a methylene group, an ethylene group, an n-propylene group, an isopropylene group, an n-butylene group, an isobutylene group, a tert-butylene group, an n-pentylene group, an isopentylene group, a neopentylene group, an n-hexylene group, an isohexylene group, a neohexylene group, a heptylene group, an octylene group, and a nonylene group. Among those, a methylene group, an ethylene group, an n-propylene group, an isopropylene group, an n-pentylene group, an isopentylene group, and a neopentylene group are preferred, and an ethylene group, an n-propylene group, an n-butylene group, an n-pentylene group, and a neopentylene group are more preferred, from a perspective of prevention of deposition of an insoluble component, stability, and the like at the time of preparing the resin precursor or the like.

$n^1$ and n-independently represent an integer from 0 to 3. From a perspective of prevention of deposition of an insoluble component at the time of preparing the resin precursor or the like, and availability, $n^1$ and $n^2$ are preferably 1 or 2, more preferably, 1.

A mono-, bi-, tri-, or higher functional fluorine-containing (meth)acrylate is exemplified as a fluorine-containing (meth)acrylate compound. Among those, a bifunctional fluorine-containing (meth)acrylate is preferred from a perspective of availability. A compound represented by Formula (3) given below is exemplified as a bifunctional fluorine-containing (meth)acrylate.

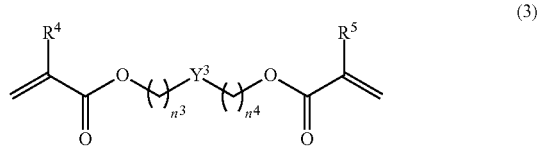

(3)

(In the formula, $R^4$ and $R^5$ independently represent a hydrogen atom or a methyl group, $Y^3$ represents a $C_{2\ to\ 12}$ perfluoroalkylene group, or —(CF$_2$—O—CF$_2$)$_z$—, $n^3$ and $n^4$ independently represent an integer from 1 to 12, and z represents an integer from 1 to 4.)

$R^4$ and $R^5$ independently represent a hydrogen atom or a methyl group. Among those, a hydrogen atom is preferred.

$Y^3$ represents a $C_{2\ to\ 12}$ perfluoroalkylene group or —(CF$_2$—O—CF$_2$)$_z$—, and z represents an integer from 1 to 4. A perfluoroalkylene group may be linear or branched. A perfluoroalkylene group is preferably —(CF$_2$)—, —(CF$_2$CF$_2$)—, —(CF$_2$CF$_2$CF$_2$)—, or —(CF$_2$CF$_2$CF$_2$CF$_2$)—.

$n^3$ and $n^4$ independently represent an integer from 1 to 12. From a perspective of prevention of deposition of an insoluble component at the time of preparing the resin precursor or the like, and availability, the uppermost value of $n^3$ and $n^4$ is preferably 6, more preferably, 4, further more preferably, 2.

z is preferably an integer from 1 to 3, more preferably, an integer of 1 or 2.

Specific examples of a bifunctional fluorine-containing (meth)acrylate compound include 1,4-di(meth)acryloyloxy-2,2,3,3-tetrafluorobutane, 1,6-di(meth)acryloyloxy-3,3,4,4-tetrafluorohexane, 1,6-di(meth)acryloyloxy-2,2,3,3,4,4,5,5-octafluorohexane, 1,8-di(meth)acryloyloxy-3,3,4,4,5,5,6,6-octafluorooctane, 1,8-di(meth)acryloyloxy-2,2,3,3,4,4,5,5,6,6,7,7-dodecafluorooctane, 1,9-di(meth)acryloyloxy-2,2,3,3,4,4,5,5,6,6,7,7,8,8-tetradecafluorononane, 1,10-di(meth)acryloyloxy-2,2,3,3,4,4,5,5,6,6,7,7,8,8,9,9-hexadecafluorodecane, and 1,12-di(meth)acryloyloxy-2,2,3,3,4,4,5,5,6,6,7,7,8,8,9,9,10,10,11,11-icosafluorododecane. Further, an ethylene oxide modified fluorinated bisphenol A di(meth)acrylate, a propylene oxide modified fluorinated bisphenol A di(meth)acrylate, and the like may be used as a bifunctional fluorine-containing (meth)acrylate.

Among those, a bifunctional fluorine-containing (meth)acrylate compound is preferably 1,6-di(meth)acryloyloxy-2,2,3,3,4,4,5,5-octafluorohexane, more preferably, a compound represented by Formula (3-1) given below (1,6-diacryloyloxy-2,2,3,3,4,4,5,5-octafluorohexane).

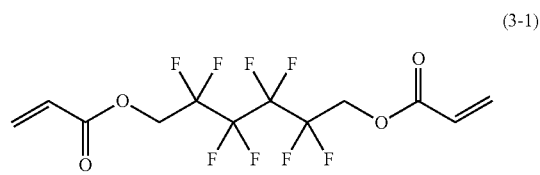 [SMILES: C=CC(=O)OCC(F)(F)C(F)(F)C(F)(F)C(F)(F)COC(=O)C=C]

(3-1)

A content amount of a fluorine-containing (meth)acrylate compound in the resin precursor is not particularly limited. However, from a perspective of an optical characteristic such as an abbe number, compatibility with the compound (1), and the like, the uppermost value of a total amount of a fluorine-containing (meth)acrylate compound is preferably 50 mass %, more preferably, 45 mass %, further more preferably, 42 mass %. The lowermost value of the total amount is preferably 20 mass %, more preferably 30 mass %, further more preferably, 35 mass %.

Examples of a (meth)acrylate compound having a fluorene structure include a monofunctional (meth)acrylate compound having a fluorene structure, a bifunctional (meth)acrylate compound having a fluorene structure, and a tri- or higher functional (meth)acrylate compound having a fluorene structure. Among those, a bifunctional (meth)acrylate compound having a fluorene structure is preferred from a perspective of availability. Specific examples of such compound include a compound represented by Formula (4) given below and a compound represented by Formula (5) given below.

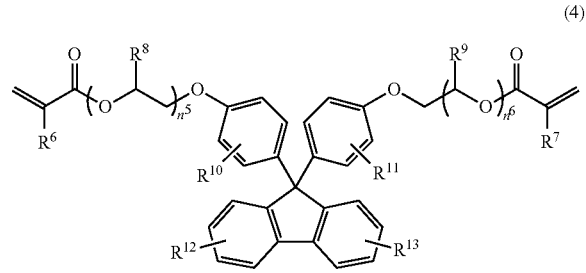

(4)

(In the formula, $R^6$ and $R^7$ independently represent a hydrogen atom or a methyl group, $R^8$ and $R^9$ independently represent a hydrogen atom, a methyl group, or an ethyl group, $R^{10}$, $R^{11}$, $R^{12}$, and $R^{13}$ independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group, and $n^5$ and $n^6$ independently represent an integer from 0 to 3.)

(5)

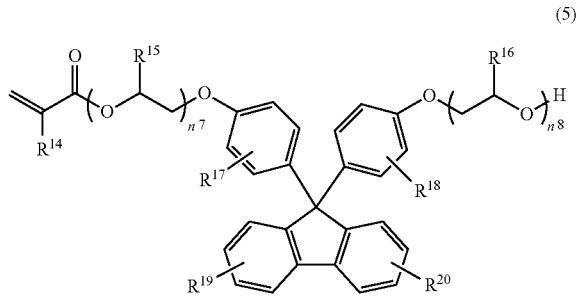

(In the formula, $R^{14}$ represents a hydrogen atom or a methyl group, $R^{15}$ and $R^{16}$ independently represent a hydrogen atom, a methyl group, or an ethyl group, $R^{17}$, $R^{18}$, $R^{19}$, and $R^{20}$ independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group, $n^7$ and $n^8$ independently represent an integer from 0 to 3.)

Formula (4) is described.

$R^6$ and $R^7$ independently represent a hydrogen atom or a methyl group. Among those, a hydrogen atom is preferred.

$R^8$ and $R^9$ independently represent a hydrogen atom, a methyl group, or an ethyl group. Among those, from a perspective of availability, a hydrogen atom is preferred.

$R^{10}$, $R^{11}$, $R^{12}$ and $R^{13}$ independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group.

As a $C_{1\ to\ 6}$ alkyl group, a linear, branched, or cyclic alkyl group may be provided. From a perspective of availability, a linear or a branched alkyl group is preferred. Specific examples of a $C_{1\ to\ 6}$ alkyl group include a methyl group, an ethyl group, an n-propyl group, an isopropyl group, an n-butyl group, an isobutyl group, a tert-butyl group, an n-pentyl group, an isopentyl group, a neopentyl group, an n-hexyl group, an isohexyl group, a neohexyl group, a cyclopropyl group, a cyclobutyl group, a cyclopentyl group, and a cyclohexyl group. Among those, a methyl group and an ethyl group are preferred.

A phenyl group in which a hydrogen atom may be replaced with a fluorine atom or a $C_{1\ to\ 6}$ alkyl group is obtained by replacing part or an entirety of a hydrogen atom in a phenyl group with a fluorine atom or a $C_{1\ to\ 6}$ alkyl group. As a $C_{1\ to\ 6}$ alkyl group as described above, a methyl group and an ethyl group are preferred from a perspective of availability.

$n^5$ and $n^6$ independently represent an integer from 0 to 3. Among those, $n^5$ and $n^6$ are preferably an integer from 0 to 2, more preferably, 0 or 1, further more preferably, 1, from a perspective of high hardness and transparency, and an excellent optical characteristic.

Formula (5) is described.

$R^{14}$ represents a hydrogen atom or a methyl group. Among those, a hydrogen atom is preferred.

$R^{15}$ and $R^{16}$ independently represent a hydrogen atom, a methyl group, or an ethyl group. Among those, from a perspective of availability, a hydrogen atom is preferred.

$R^{17}$, $R^{18}$, $R^{19}$ and $R^{20}$ independently represent a hydrogen atom, a fluorine atom, a $C_{1\ to\ 6}$ alkyl group, or a phenyl group in which a hydrogen atom may be replaced with a fluorine atom or a $C_{1\ to\ 6}$ alkyl group.

As a $C_{1\ to\ 6}$ alkyl group, a linear, branched, or cyclic alkyl group may be provided. From a perspective of availability, a linear or a branched alkyl group is preferred. Specific examples of a $C_{1\ to\ 6}$ alkyl group include a methyl group, an ethyl group, an n-propyl group, an isopropyl group, an n-butyl group, an isobutyl group, a tert-butyl group, an n-pentyl group, an isopentyl group, a neopentyl group, an n-hexyl group, an isohexyl group, a neohexyl group, a cyclopropyl group, a cyclobutyl group, a cyclopentyl group, and a cyclohexyl group. Among those, a methyl group and an ethyl group are preferred.

A phenyl group in which a hydrogen atom may be replaced with a fluorine atom or a $C_{1\ to\ 6}$ alkyl group is obtained by replacing part or an entirety of a hydrogen atom in a phenyl group with a fluorine atom or a $C_{1\ to\ 6}$ alkyl group. As such a phenyl group in which a hydrogen atom may be replaced with a $C_{1\ to\ 6}$ alkyl group described above, a phenyl group, a methylphenyl group, an ethylphenyl group are preferred from a perspective of availability.

$n^7$ and $n^8$ independently represent an integer from 0 to 3. Among those, $n^7$ and $n^8$ are preferably an integer from 0 to 2, more preferably, 0 or 1, further more preferably, 1, from a perspective of high hardness and transparency, and an excellent optical characteristic.

Specific examples of a (meth)acrylate compound having a fluorene structure preferably include a compound represented by Formula (4-1) given below and a compound represented by Formula (5-1) given below, more preferably, a compound (9,9-bis [4-(2-acryloyloxyethoxy)phenyl]fluorene) represented by Formula (4-1) given below.

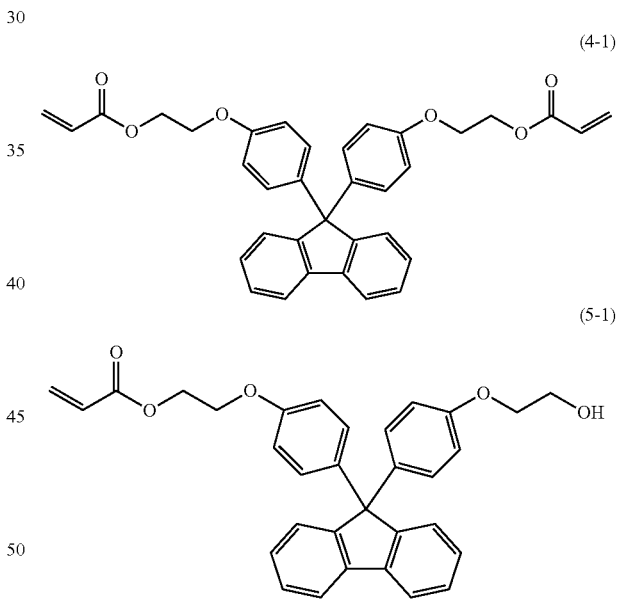

A content amount of a (meth)acrylate compound having a fluorene structure in the resin precursor is not particularly limited. However, from a perspective of prevention of white turbidity and prevention of deposition of an insoluble component, a total amount of a (meth)acrylate compound having a fluorene structure is preferably 20 to 50 mass %. The uppermost content amount is more preferably 40 mass %, further more preferably, 35 mass %. The lowermost content amount is more preferably 25 mass %, further more preferably, 26 mass %.

As a di(meth)acrylate compound other than each component described above, a compound having two (meth)acrylate structures is exemplified. Specific examples of a di(meth)acrylate compound include a 2-ethyl-2-butyl-propanediol (meth)acrylate, a 1,3-butyleneglycoldi(meth)acrylate, a 1,6-hexanedioldi(meth)acrylate, a 1,9-nonanediol (meth)acrylate, a 1,10-decanedioldi(meth)acrylate, a neopentylglycoldi(meth)acrylate, a dipropyleneglycoldi(meth)acrylate, a glyceroldi(meth)acrylate, an ethylene oxide modified neopentylglycoldi(meth)acrylate, a propylene oxide modified neopentylglycoldi(meth)acrylate, an ethylene oxide modified bisphenol A di(meth)acrylate, a propylene oxide modified bisphenol A di(meth)acrylate, an ethylene oxide/propylene oxide modified bisphenol A di(meth)acrylate, and a butylethylpropanedioldi(meth)acrylate.

Among those di(meth)acrylate compounds, an aliphatic di(meth)acrylate is preferred, from a perspective of compatibility with the compound (1) and the like. Among those, a 2-ethyl-2-butyl-propanediol (meth)acrylate, a 1,3-butyleneglycoldi(meth)acrylate, and a 1,6-hexanedioldi(meth)acrylate are preferred, and 1,6-hexanediol diacrylate (AHDN) is preferred more. An aliphatic di(meth)acrylate has a chemical structure that achieves high compatibility with the compound (1), and hence a stable liquid state can be maintained. As a result, the resin precursor in a liquid state, which contains the compound (1) in high concentration can be achieved. When used as an optical material, the resin precursor containing the compound (1) in high concentration can further exert an effect relating to an optical characteristic.

A content amount of a di(meth)acrylate compound in the resin precursor is not particularly limited. However, from a perspective of compatibility with the compound (1) and the like, a total amount of a di(meth)acrylate compound is preferably 10 to 80 mass %. The uppermost content amount is more preferably 60 mass %, further more preferably, 50 mass %. The lowermost content amount is more preferably 20 mass %, further more preferably, 35 mass %.

The curable composition according to the present embodiment may contain a component other than those described above. A monofunctional (meth)acrylate, a trifunctional (meth)acrylate, and a tetrafunctional (meth)acrylate are exemplified. By using those together, hardness, transparency, and an optical characteristic of the resin can be adjusted. Among those, a monofunctional (meth)acrylate is preferred, from a perspective of improving compatibility with the compound (1).

Examples of a monofunctional (meth)acrylate include a methyl(meth)acrylate, ethyl(meth)acrylate, a butyl(meth)acrylate, an isodecyl(meth)acrylate, a lauryl(meth)acrylate, a tridecyl(meth)acrylate, an acetyl(meth)acrylate, a stearyl(meth)acrylate, a tert-butyl(meth)acrylate, a 2-ethylhexyl(meth)acrylate, a 2-hydroxybutyl(meth)acrylate, a 2-hydroxyethyl(meth)acrylate, a 2-hydroxypropyl(meth)acrylate, a 3-methoxybutyl(meth)acrylate, a diethylaminoethyl(meth)acrylate, a phenoxypolyethyleneglycol(meth)acrylate, an isostearyl(meth)acrylate, a paracumylphenoxyethyleneglycol(meth)acrylate, a dimethylaminoethyl(meth)acrylate, a 2-ethylhexylcarbitol(meth)acrylate, a butoxyethyl(meth)acrylate, an ethoxydiethyleneglycol(meth)acrylate, a lauroxypolyethyleneglycol(meth)acrylate, a polyethyleneglycol(meth)acrylate, a methoxydipropyleneglycolacrylate, a methoxytrypropyleneglycolacrylate, an ethoxydipropyleneglycolacrylate, an ethoxytrypropyleneglycolacrylate, a polypropyleneglycol(meth)acrylate, an acryloxypolyethyleneglycol(meth)acrylate, a stearoxypolyethyleneglycol(meth)acrylate, an octoxypolyethyleneglycol-polypropyleneglycol (meth)acrylate, a poly(propyleneglycol-tetramethyleneglycol) (meth)acrylate, a poly(ethyleneglycol-tetramethyleneglycol) (meth)acrylate, a methoxypolyethyleneglycol(meth)acrylate, a methoxypolypropyleneglycol(meth)acrylate, and a benzil(meth)acrylate. Among those, methoxytrypropyleneglycolacrylate and ethoxytrypropyleneglycolacrylate are preferred, from a perspective of a structure regarding compatibility with the compound (1) and the like.

Examples of a trifunctional (meth)acrylate includes a tris(acryloxyethyl)isocyanurate, a tris(methacryloxyethyl)isocyanurate, an epichlorohydrin modified glyceroltri(meth)acrylate, an ethylene oxide modified glyceroltri(meth)acrylate, a propylene oxide modified glyceroltri(meth)acrylate, a caprolactone modified trimethylolpropanetri(meth)acrylate, an ethylene oxide modified trimethylolpropanetri(meth)acrylate, a propylene oxide modified trimethylolpropanetri(meth)acrylate, a pentaerythritoltri(meth)acrylate, and a trimethylolpropanetri(meth)acrylate. Among those, a pentaerythritoltri(meth)acrylate is preferred, from a perspective of a structure regarding compatibility with the compound (1) and the like.

As a tetrafunctional (meth)acrylate, a pentaerythritol tetra(meth)acrylate, a dipentaerythritol hydroxypenta(meth)acrylate, and a ditrimethylolpropane tetra(meth)acrylate are exemplified. Among those, a dipentaerythritol hydroxypenta(meth)acrylate is preferred, from a perspective of a structure regarding compatibility with the compound (1) and the like.

When the resin precursor according to the present embodiment is photocurable, the resin precursor may further contain a photopolymerization initiator. The photopolymerization initiator is not particularly limited as long as polymerization of monomeric components can be initiated with light irradiation, and a publicly-known photopolymerization initiator used for photo-curing a resin may be used. Light used for light irradiation may be selected as appropriate in accordance with a photopolymerization initiator to be used, and visible light, ultraviolet light, an electron beam, and the like are generally used.

A content amount of the photopolymerization initiator depends on a type of used components or a type of irradiation light, and, in general, is preferably 0.1 to 5 mass %.

As the photopolymerization initiator, for example, a phosphine-based or acetophenone-based photopolymerization initiator is preferred, from a perspective of reactivity. As a phosphine-based photopolymerization initiator, a bis(2-4-6-trimethylbenzoyl)-phenylphosphineoxide, a 2,4,6-trimethylbenzoyl-diphenyl-phosphineoxide, and the like are preferred. As an acetophenone-based photopolymerization initiator, alkylphenyl ketones having a hydroxyl group at the alpha-position are preferred, and a 1-hydroxy-cyclohexyl-phenyl-ketone, a 2-hydroxy-2-methyl-1-phenyl-propane-1-one, and the like are more preferred, from a perspective of prevention of yellowing of a resin in addition to a perspective of reactivity.

The resin precursor according to the present embodiment may further contain a photostabilizer. A publicly-known photostabilizer may be used as the photostabilizer. Suitable examples of the photostabilizer include a hindered amine based material such as a bis(2,2,6,6-tetramethyl-4-piperidyl) sebacate, a bis(1,2,2,6,6-pentamethyl-4-piperidyl) sebacate, and a methyl-1,2,2,6,6-pentamethyl-4-piperidylsebacate.

The resin precursor according to the present embodiment may further contain a polymerization-inhibitor. A publicly-known polymerization-inhibitor may be used as the polymerization-inhibitor. Suitable examples of the polymerization-inhibitor include hydroquinones such as a p-benzoquinone, a hydroquinone, a hydroquinonemonomethylether, and a 2,5-diphenylparabenzoquinone, substituted catechols such as a T-butyl catechol, a phenothiazine, amines such as a diphenylamine, N-oxy radicals such as a tetramethylpiperidinyl-N-oxy radical (TEMPO), a nitrosobenzene, a picric acid, molecular oxygen, and sulfur. Among those, hydroquinones, a phenothiazine, and N-oxy radicals are more preferred, from a perspective of versatility and prevention of polymerization.

The resin precursor according to the present embodiment may further contain an ultraviolet light absorber. A publicly-known ultraviolet light absorber may be used as the ultraviolet light absorber. Suitable examples include a 2-(2-hydroxy-5-tert-octylphenyl)-2H-benzotriazole. When used together with the photostabilizer, the ultraviolet light absorber can be expected to exert a further excellent effect.

As suitable combinations of the components described above for the curable composition that is used together with the compound (1), the curable composition preferably contain a fluorine-containing (meth)acrylate compound or a (meth)acrylate compound having a fluorene structure, and a di(meth)acrylate compound, more preferably, a fluorine-containing (meth)acrylate compound and a di(meth)acrylate compound, further more preferably, an aliphatic fluorine-containing (meth)acrylate compound and an aliphatic di(meth)acrylate compound.

As a specific component combination of the suitable combinations described above, the curable composition preferably contains any one selected from a group consisting of a 9,9-bis [4-(2-acryloyloxyethoxy)phenyl]fluorene, a methoxytrypropyleneglycolacrylate, a 1,6-di(meth)acryloyloxy-2,2,3,3,4,4,5,5-octafluorohexane, a 1-hydroxy-cyclohexyl-phenyl-ketone, a bis(2-4-6-trimethylbenzoyl)-phenylphosphineoxide, a bis(1,2,2,6,6-pentamethyl-4-piperidyl) sebacate, a methyl 1,2,2,6,6-pentamethyl-4-piperidylsebacate, a 2-(2-hydroxy-5-tert-octylphenyl)-2H-benzotriazole, and a 1,6-hexanediol diacrylate.

Among those, it is more preferred that one or more kinds selected from a group consisting of a 1,6-di(meth)acryloyloxy-2,2,3,3,4,4,5,5-octafluorohexane, a 9,9-bis [4-(2-acryloyloxyethoxy)phenyl]fluorene, and a 1,6-hexanediol diacrylate be contained, from a perspective of effective prevention of deposition of an insoluble component and easy preparation for a stable liquid-state composition. Further, it is further more preferred that two or more kinds selected from a group consisting of a 1,6-di(meth)acryloyloxy-2,2,3,3,4,4,5,5-octafluorohexane, a 9,9-bis [4-(2-acryloyloxyethoxy)phenyl]fluorene, and a 1,6-hexanediol diacrylate be contained. Further, it is further more preferred that a 1,6-di (meth)acryloyloxy-2,2,3,3,4,4,5,5-octafluorohexane, a 9,9-bis [4-(2-acryloyloxyethoxy)phenyl]fluorene, and a 1,6-hexanediol diacrylate be contained. When such component is used together with the compound (1), preparation is further facilitated to obtain a liquid-state composition having high stability under an ordinary temperature.

In addition to the combination of the curable composition described above, it is preferred that the compound (2) be also used together. With this, an achievable range of an optical characteristic is broadened, and a degree of design freedom for a product using the compound can be improved.

A content amount of the compound (1) in the resin precursor is not particularly limited. However, from a perspective of maintaining high stability in a liquid state, the content amount is preferably 10 to 90 mass %. From the perspective described above, the uppermost content amount is more preferably 50 mass %, further more preferably, 30 mass %, still further more preferably, 25 mass %. The lowermost content amount is more preferably 15 mass %.

<Cured Object>

A cured object can be obtained by curing the resin precursor according to the present embodiment. A curing method may be photocuring or thermocuring, depending on a property of the contained curable composition. As the curing method, for example, a method of using an ultraviolet-light curable composition and performing irradiation of ultraviolet light may be employed.

As a physical property of the cured object, a $\theta_{g,F}$ value is preferably 0.5 or greater, more preferably, 0.6 or greater, further more preferably, 0.7 or greater, still further more preferably, 0.8 or greater. The lowermost value of an abbe number ($v_d$) is preferably 10 or greater, more preferably, 15 or greater, further more preferably, 17 or greater. The uppermost value of an abbe number ($v_d$) is preferably 40 or less, more preferably, 30 or less, further more preferably, 27 or less. A numerical range of an abbe number ($v_d$) is preferably 10 or greater and 40 or less. Further, it is preferred that both the $\theta_{g,F}$ value and the abbe number ($v_d$) respectively satisfy the numerical ranges described above. A refractive index ($n_d$) with respect to a d-line may be 1.50 or greater and 1.65 or less.

A glass material and an optical material formed of an organic resin or the like have a tendency of reducing a refractive index as approaching a small wavelength side. As an index indicating a wavelength dispersion characteristic of a refractive index, the $\theta_{g,F}$ value and the abbe number ($v_d$) are used. These values are unique to optical materials. In a refraction optical system, reduction in chromatic aberration has been attempted by appropriately combining optical materials having different dispersion characteristics. However, when the configuration or the number of lenses is limited from a perspective of design requirement or the like, it is difficult to correct chromatic aberration sufficiently in some cases. In view of this, the cured object according to the present embodiment has a high $\theta_{g,F}$ value, and has a unique dispersion characteristic. The cured object according to the present embodiment has such property, and hence has an excellent chromatic aberration correction function. Thus, such problem can be solved.

Further, an inner transmittance of the cured object is preferably 80% or greater over a wavelength range from 400 nm to 450 nm. According to the present embodiment, the cured object having a high inner transmittance can be obtained as an optical material.

<Optical Element, Optical System, Interchangeable Camera Lens, Optical Device, and the Like>

The cured object according to the present embodiment may be used as an optical element. The optical element including the cured object includes a mirror, a lens, a prism, and a filter. Suitable usage examples include an optical lens. Further, the optical element according to the present embodiment may be used for an optical system including the optical element.

The optical system according to the present embodiment may be suitably used for an interchangeable camera lens including the optical system. Publicly-known configurations may be employed for the optical element, the optical lens, and the interchangeable camera lens. Further, the optical system according to the present embodiment may be suitably used for an optical device including the optical system. The optical device including the optical system is not particularly limited, and examples thereof include an imaging device such as a lens-interchangeable camera and a fixed lens camera, and an optical microscope.

(Imaging Device)

FIG. 1 is a perspective view of one example of an optical device according to the present embodiment as an imaging device.

An imaging device 1 is a so-called digital single-lens reflex camera (a lens-interchangeable camera), and a photographing lens (an optical system) 103 includes the cured object according to the present embodiment. A lens barrel 102 is mounted to a lens mount (not illustrated) of a camera body 101 in a removable manner. Further, an image is formed with light, which passes through the lens 103 of the lens barrel 102, on a sensor chip (solid-state imaging elements) 104 of a multi-chip module 106 arranged on a back surface side of the camera body 101. The sensor chip 104 is a so-called bare chip such as a CMOS image sensor, and the multi-chip module 106 is, for example, a Chip On Glass (COG) type module including the sensor chip 104 being a bare chip mounted on a glass substrate 105.

Figure 2:
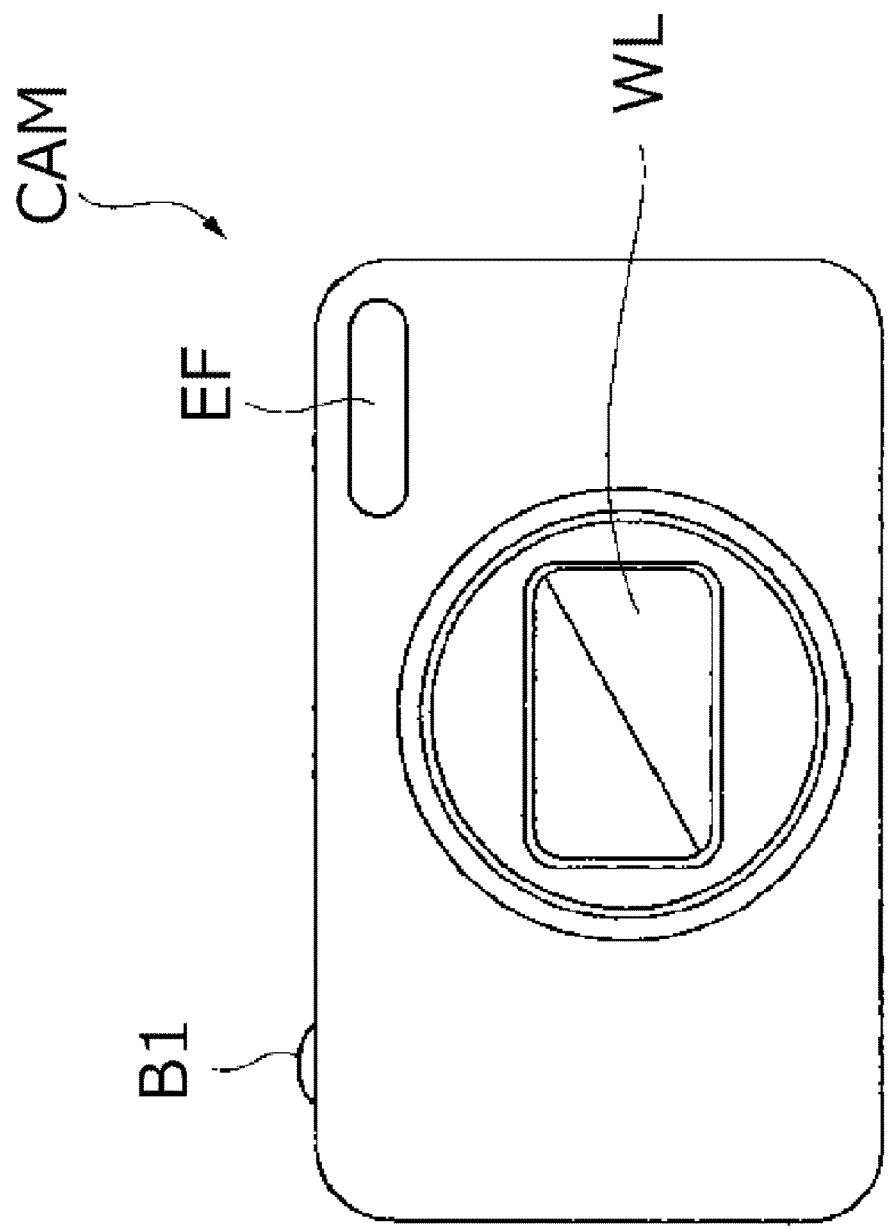
FIG. 2 is a front view of another example of the optical device according to the present embodiment as an imaging device.
Figure 3:
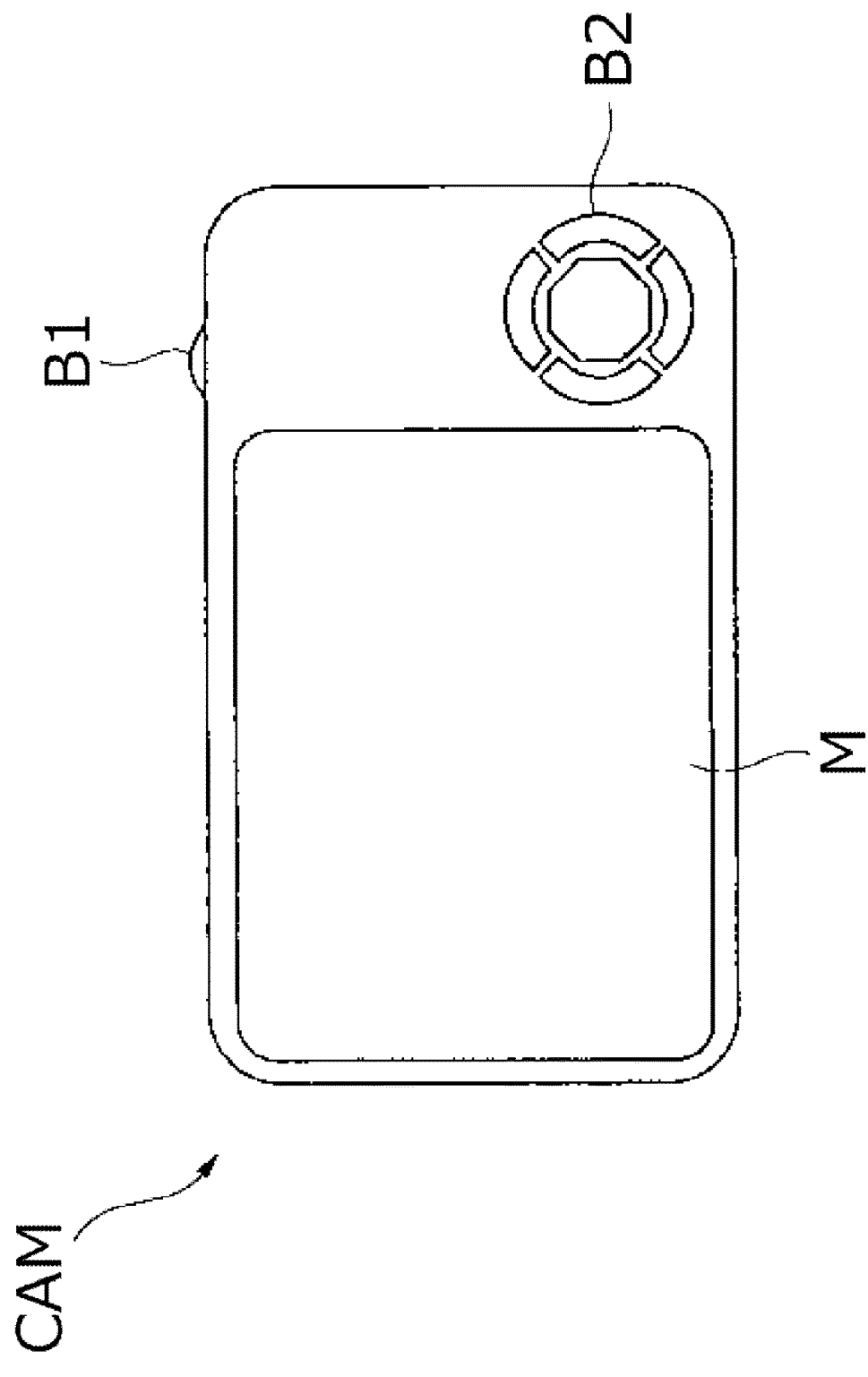
FIG. 3 is a back view of the imaging device of FIG. 2.

FIG. 2 is a front view of another example of the optical device according to the present embodiment as an imaging device. FIG. 3 is a back view of the imaging device.

The imaging device CAM is a so-called digital still camera (a fixed lens camera), and a photographing lens (an optical system) WL includes the cured object according to the present embodiment. When a power button (not illustrated) of the imaging device CAM is pressed, a shutter (not illustrated) of the photographing lens WL is opened, light from an object to be imaged (a body) is converged by the photographing lens WL and forms an image on imaging elements arranged on an image surface. An object image formed on the imaging elements is displayed on a liquid crystal monitor M arranged on the back of the imaging device CAM. A photographer decides composition of the object image while viewing the liquid crystal monitor M, then presses down a release button B1, and captures the object image on the imaging elements. The object image is recorded and stored in a memory (not illustrated). For example, an auxiliary light emitting unit EF that emits auxiliary light in a case that the object is dark and a function button B2 to be used for setting various conditions of the imaging device CAM and the like are arranged on the imaging device CAM.

A higher resolution, lighter weight, and a smaller size are demanded for the optical system to be used in such digital camera or the like. In order to achieve such demands, it is effective to use optical glass with a high refractive index as the optical system. From such viewpoint, the optical glass according to the present embodiment is suitable as a member of such optical device. Note that, in addition to the imaging device described above, examples of the optical device to which the present embodiment is applicable include a projector and the like. In addition to the lens, examples of the optical element include a prism.

(Multi-Photon Microscope)

Figure 4:
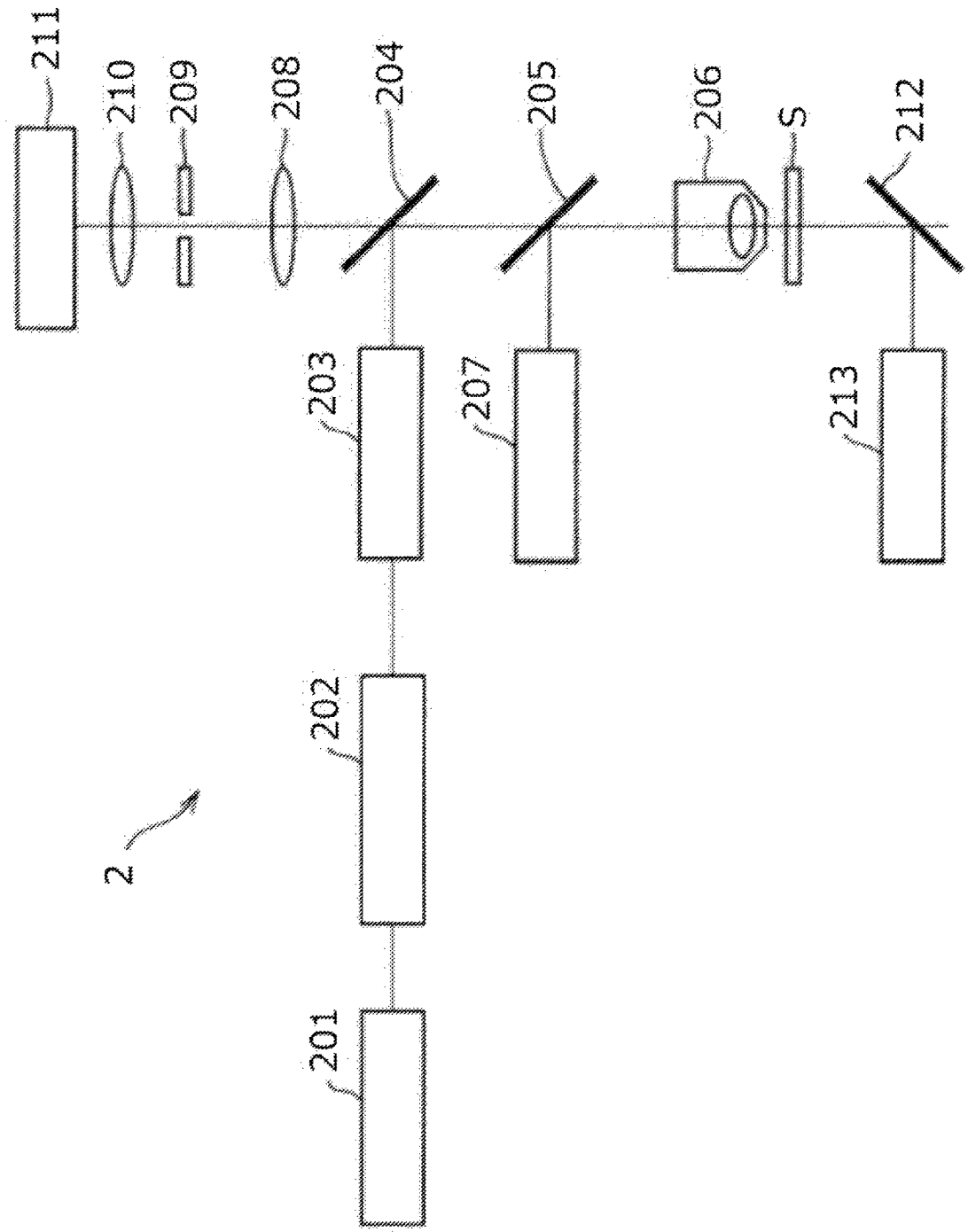
FIG. 4 is a block diagram illustrating one example of the optical device according to the present embodiment as a multi-photon microscope.

FIG. 4 is a block diagram illustrating one example of the optical device according to the present embodiment as a multi-photon microscope.

The multi-photon microscope 2 includes an objective lens 206, a condensing lens 208, and an image forming lens 210, as optical elements. Hereinafter, description is mainly made on the optical system of the multi-photon microscope 2.

A pulse laser device 201 emits ultrashort pulse light having, for example, a near infrared wavelength (approximately 1,000 nm) and a pulse width of a femtosecond unit (for example, 100 femtoseconds). In general, ultrashort pulse light immediately after being emitted from the pulse laser device 201 is linearly polarized light that is polarized in a predetermined direction.

A pulse division device 202 divides the ultrashort pulse light, increases a repetition frequency of the ultrashort pulse light, and emits the obtained light.

A beam adjustment unit 203 has a function of adjusting a beam diameter of the ultrashort pulse light, which enters from the pulse division device 202, to a pupil diameter of the objective lens 206, a function of adjusting convergence and divergence angles of the ultrashort pulse light in order to correct chromatic aberration (a focus difference) on an axis of a wavelength of multi-photon excitation light emitted from a sample S and the wavelength of the ultrashort pulse light, a pre-chirp function (group velocity dispersion compensation function) providing inverse group velocity dispersion to the ultrashort pulse light in order to correct increased of the pulse width of the ultrashort pulse light due to group velocity dispersion at the time of passing through the optical system, and the like.

The ultrashort pulse light emitted from the pulse laser device 201 has a repetition frequency increased by the pulse division device 202, and is adjusted as mentioned above by the beam adjustment unit 203. Furthermore, the ultrashort pulse light emitted from the beam adjustment unit 203 is reflected on a dichroic mirror 204 in a direction toward a dichroic mirror 205, passes through the dichroic mirror 205, is converged by the objective lens 206, and is radiated to the sample S. At this time, an observation surface of the sample S may be scanned with the ultrashort pulse light through use of a scanning means (not illustrated).

For example, when the sample S is subjected to fluorescence imaging, a fluorescent pigment by which the sample S is dyed is subjected to multi-photon excitation in an irradiated region with the ultrashort pulse light and the vicinity thereof on the sample S, and fluorescence having a wavelength shorter than an infrared wavelength of the ultrashort pulse light (hereinafter, also referred to "observation light") is emitted.

The observation light emitted from the sample S in a direction toward the objective lens 206 is collimated by the objective lens 206, and is reflected on the dichroic mirror 205 or passes through the dichroic mirror 205 depending on the wavelength.

The observation light reflected on the dichroic mirror 205 enters a fluorescence detection unit 207. The fluorescence detection unit 207 is formed of, for example, a barrier filter, a photo multiplier tube (PMT), or the like, receives the observation light reflected on the dichroic mirror 205, and outputs an electronic signal depending on an amount of the light. The fluorescence detection unit 207 detects the observation light over the observation surface of the sample S, in conformity with the ultrashort pulse light scanning on the observation surface of the sample S.

Meanwhile, the observation light passing through the dichroic mirror 205 is de-scanned by a scanning means (not illustrated), passes through the dichroic mirror 204, is converged by the condensing lens 208, passes through a pinhole 209 provided at a position substantially conjugate to a focal position of the objective lens 206, passes through the image forming lens 210, and enters a fluorescence detection unit 211.

The fluorescence detection unit 211 is formed of, for example, a barrier filter, a PMT, or the like, receives the observation light forming an image on a reception surface of the fluorescence detection unit 211 by the image forming lens 210, and outputs an electronic signal depending on an amount of the light. The fluorescence detection unit 211 detects the observation light over the observation surface of the sample S, in conformity with the ultrashort pulse light scanning on the observation surface of the sample S.

Note that, all the observation light emitted from the sample S in a direction toward the objective lens 206 may be detected by the fluorescence detection unit 211 by excluding the dichroic mirror 205 from the optical path.

The observation light emitted from the sample S in a direction opposite to the objective lens 206 is reflected on a dichroic mirror 212, and enters a fluorescence detection unit 213. The fluorescence detection unit 213 is formed of, for example, a barrier filter, a PMT, or the like, receives the observation light reflected on the dichroic mirror 212, and outputs an electronic signal depending on an amount of the light. The fluorescence detection unit 213 detects the observation light over the observation surface of the sample S, in conformity with the ultrashort pulse light scanning on the observation surface of the sample S.

The electronic signals output from the fluorescence detection units 207, 211, and 213 are input to, for example, a computer (not illustrated). The computer is capable of generating an observation image, displaying the generated observation image, storing data on the observation image, based on the input electronic signals.

<Cemented Lens and Method for Manufacturing Cemented Lens>

A case where the compound, the resin precursor, and the cured object according to the present embodiment are used for a single lens is mainly described above. The compound, the resin precursor, the cured object and the like according to the present embodiment may be suitably used as a joining member of a cemented lens including a plurality of lenses.

Figure 5:
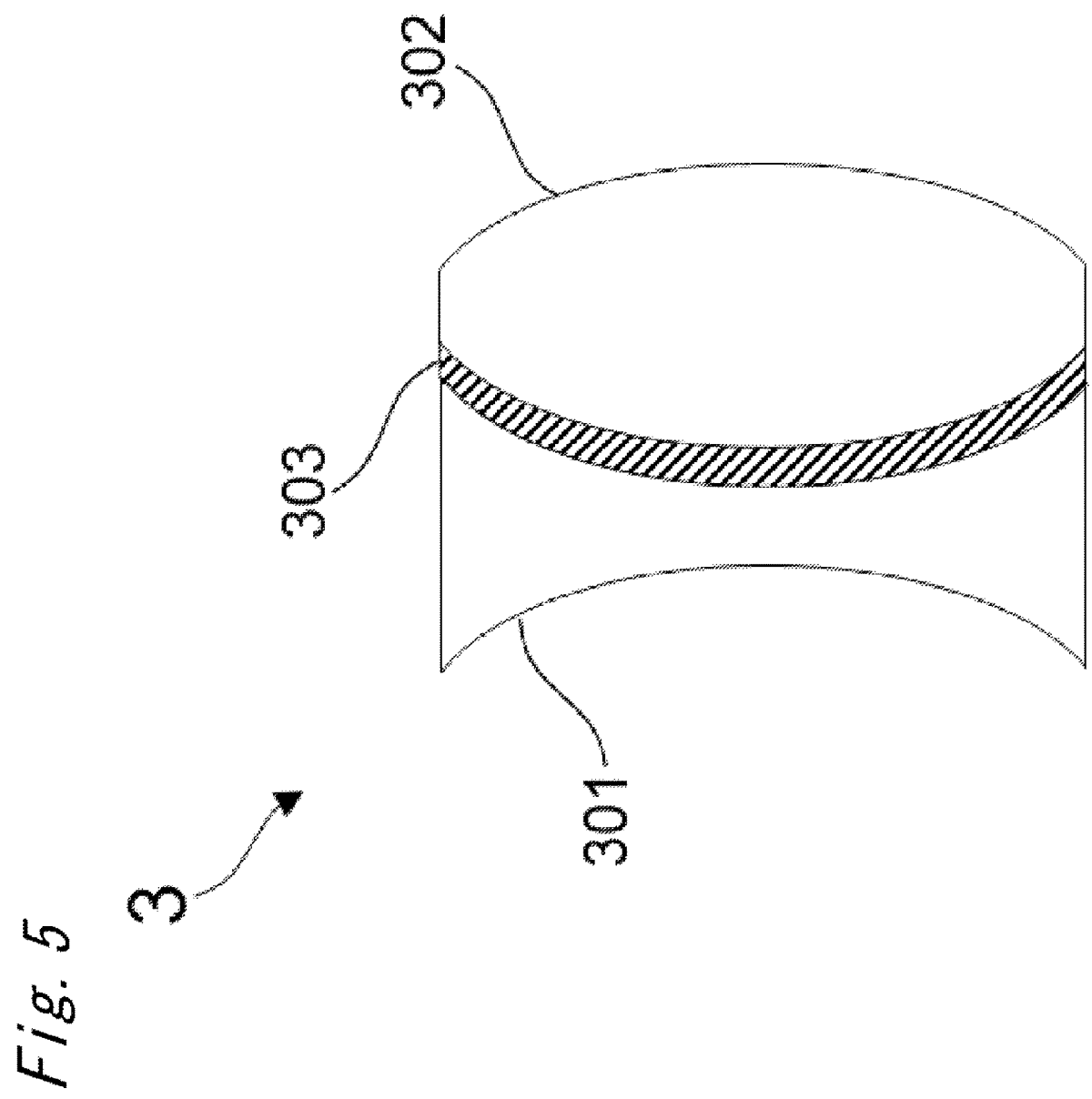
FIG. 5 is a schematic view illustrating one example of a cemented lens according to the present embodiment.

FIG. 5 is a schematic view illustrating one example of the cemented lens according to the present embodiment.

A cemented lens 3 includes a first lens element 301 and a second lens element 302 joined with each other through intermediation of the cured object 303 according to the present embodiment. Note that, the lenses forming the cemented lens are referred to as "lens elements" as described above in some cases from a viewpoint of clearly stating that the lenses are the elements of the cemented lens. In this manner, the cured object 303 according to the present embodiment can be caused to function as the joining member described above.

When the compound, the resin precursor, and the cured object according to the present embodiment are used for a cemented lens including two lens elements, there is exemplified a manufacturing method including, firstly, (1) a contacting step of contacting the first lens element and the second lens element with each other through intermediation of the resin precursor according to the present embodiment, and (2) a joining step of curing the resin precursor to join the first lens element and the second lens element with each other.

(1) In the contacting step, the resin precursor according to the present embodiment is interposed in a pre-cured state between the first lens element and the second lens element. For example, when the resin precursor is a liquid-state composition, the resin precursor is applied on contact surfaces between the first lens element and the second lens element, and both the lens elements are laid over with each other.

(2) In the joining step, a method of curing the resin precursor may be photocuring or thermocuring. Curing is performed preferably by irradiating the resin precursor with light. The resin precursor is preferably irradiated with light through the first lens element or the second lens element. The compound, the resin precursor, and the cured object according to the present embodiment can prevent yellowing due to aging, and can maintain high transparency for a long period of time. From this perspective, the manufacturing method is suitable.

The cementing lens thus obtained may be used for an optical system, similarly as described with the single lens. The cemented lens according to the present embodiment may be suitably used for an optical device including an interchangeable camera lens and an optical system, similarly as described with the single lens. Note that, in the aspect described above, description is made on the cemented lens using the two lens elements. The present invention is however not limited thereto, and a cemented lens using three or more lens elements may be used. When a cemented lens using three or more lens elements is obtained, the cured object according to the present embodiment may be applied to all the joining members between the lens elements. However, the present invention is not limited thereto, and the cured object according to the present embodiment is only required to be applied to at least one of the joining members.

EXAMPLES

The present invention is further described in detail with Examples and Comparative Examples given below. However, the following examples are not intended to limit the present invention at all. First, compounds were synthesized, resin precursors containing those compounds and cured objects obtained therefrom were produced, and physical property evaluation was performed on each resultant.

I. Production of Compound and Physical Property Evaluation

Example 1 (Synthesis of Compound (1A))

(Synthesis of Intermediate Compound (a))

10.00 g (30.9 mmol) of 2-[2-hydroxy-5-[2-(methacryloyloxy)ethyl]phenyl-2H-benzotriazole, 200 mg (1.61 mmol) of 4-methoxyphenol (MEHQ), and 100 mL of tetrahydrofuran (THF, dehydration) were measured and put in a 300 milliliter-reactor vessel, and the resultant was stirred to obtain a uniform solution. 6.12 g (40.2 mmol) of 1,8-diazabicyclo [5.4.0]-7-undecene were dropped to the resultant. After stirring at a room temperature for an hour, 4.98 g (61.9 mmol) of chloromethyl methyl ether were slowly dropped to the resultant. Stirring was sequentially performed for two hours. After that, when the reaction solution was checked with thin layer chromatography (TLC), it was found that 2-[2-hydroxy-5-[2-(methacryloyloxy)ethyl]phenyl-2H-benzotriazole almost disappeared. At this point, 30 mL of ethyl acetate were added to the reaction solution. The resultant was replaced in a separating funnel, and was washed twice with 100 mL of a 2N sodium hydroxide aqueous solution and washed once with 100 mL of a saturated saline solution. The resultant was replaced in a vessel, and anhydrous magnesium sulfate was added.

Solid matters were removed through filtration, and the filtrate was concentrated under a low pressure at a temperature of 40 degrees Celsius. 2 mL of a chloroform solution with 1 mg/ml of MEHQ was added to the light yellow-colored liquid obtained through refining with a silica gel column (a development solvent satisfied n-hexane:ethyl acetate=3:1), and the resultant was dried under a low pressure at a temperature of 40 degrees Celsius for three hours. Thus, an intermediate compound (a) was obtained. The yield amount was 9.97 g (27.1 mmol), and the yield was 87.8%.

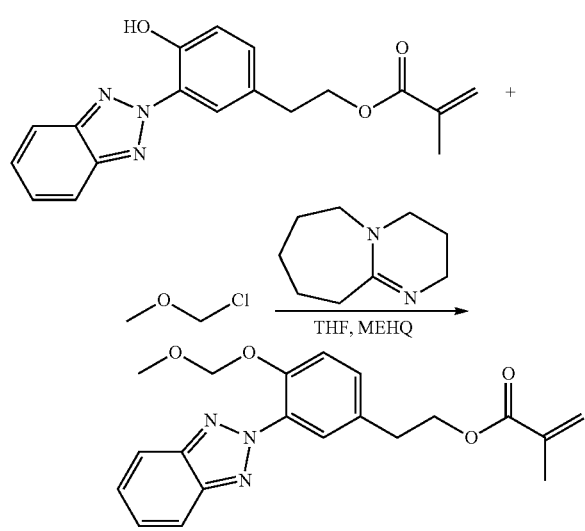

(a)

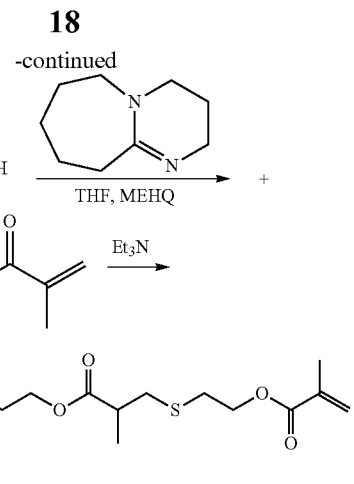

(b)

Synthesis of Compound (1A)

(Synthesis of Intermediate Compound (b))

9.97 g (27.1 mmol) of the intermediate compound (a), 199 mg (1.60 mmol) of MEHQ, and 30 mL of tetrahydrofuran (dehydration) were measured and put in a 300 milliliter-reactor vessel, and the resultant was stirred to obtain a uniform solution. A dilute solution of 2.12 g (27.1 mmol) of 2-melcaptoethanol and 6.12 g (40.2 mmol) of 1,8-diazabi-cyclo [5.4.0]-7-undecene with 5 mL of tetrahydrofuran were added to the resultant. Stirring was sequentially performed for two hours. After that, when the reaction solution was checked with TLC, the intermediate compound (a) completely disappeared, it was found that an odor of 2-melcaptoethanol also disappeared. 6.86 g (67.8 mmol) of triethylamine (Et₃N) were added and cooled to a temperature of 0 degrees Celsius. 5.67 g (54.3 mmol) of methacryloyl chloride were slowly dropped to the resultant. Stirring was sequentially performed for two hours. After that, 35 mL of a 2N sodium hydroxide aqueous solution were added to the reaction solution. The resultant was separated into an organic layer and a water layer by a separating funnel, and then the water layer was extracted twice by 20 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees of Celsius. Thus, 14.76 g of a crude product of a light yellow liquid containing the intermediate compound (b) as a main component was obtained.

14.76 g of a crude product containing the intermediate compound (b) as a main component and 90 mL of tetrahydrofuran (dehydration) were measured and put in a 200 milliliter-reactor vessel, and the resultant was stirred to obtain a uniform solution. 10 mL of 12N hydrochloric acid were slowly dropped to the resultant. Stirring was sequentially performed all night. After that, when the reaction solution was checked with TLC, it was found that the intermediate compound (b) completely disappeared. After concentration under a low pressure at a temperature of 40 degrees Celsius, 100 mL of ethyl acetate were added. The resultant was separated into an organic layer and a water layer by a separating funnel, and then the organic layer was washed three times with 100 mL of a saturated saline solution. The resultant was replaced in a vessel, and anhydrous magnesium sulfate was added.

Solid matters were removed through filtration, and the filtrate was concentrated under a low pressure at a temperature of 40 degrees Celsius. 2 mL of a chloroform solution with 1 mg/ml of MEHQ were added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a compound (1A) was obtained. The yield amount was 8.72 g (18.6 mmol), and the yield from the intermediate compound (a) to the compound (1A) through the intermediate compound (b) was 68.4%. The compound (1A) was then crystallized while being kept in a dark place. The melting point of the compound (1A) was at a temperature of 61 degrees Celsius.

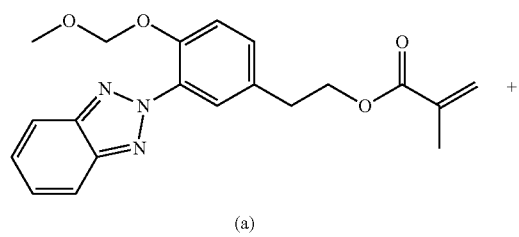

(a)

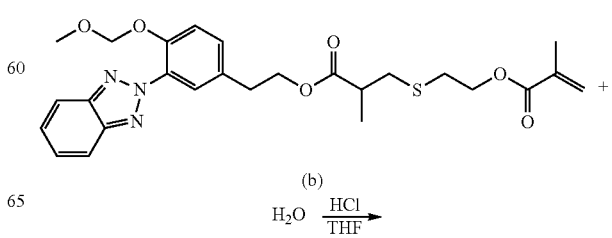

(b)

$H_2O \xrightarrow[THF]{HCl}$

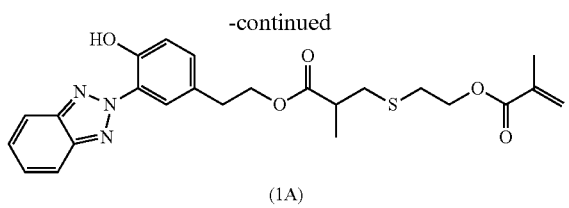

(1A)

Measurement results of ¹H-NMR ("AVANCE III HD" available from Bruker) being the compound (1A) are shown below.

¹H-NMR (500 MHz, DMSO-d6): δ1.09-1.11 (3H, d), 1.84 (3H, s), 2.61-2.78 (5H, m), 2.92-2.95 (2H, t), 4.14-4.17 (2H, t), 4.26-4.29 (2H, t), 5.65 (1H, s), 5.99 (1H, s), 7.11-7.12 (1H, d), 7.32-7.34 (1H, dd), 7.52-7.55 (2H, m), 7.77-7.78 (1H, d), 8.01-8.05 (2H, m), 10.48 (1H, s)

m.p.=61 degrees Celsius

Example 2 (Synthesis of Compound (1B))

Synthesis of Intermediate Compound (c)

The intermediate compound (a) described in Example 1 was used, and thus an intermediate compound (c) was synthesized. 9.57 g (26.0 mmol) of the intermediate compound (a), 191 mg (1.54 mmol) of MEHQ, and 30 mL of tetrahydrofuran (dehydration) were measured and put in a 300 milliliter-reactor vessel, and the resultant was stirred to obtain a uniform solution. A dilute solution of 2.40 g (26.0 mmol) of 3-mercaptopropanol and 0.198 g (1.30 mmol) of 1,8-diazabicyclo [5.4.0]-7-undecene with 5 mL of tetrahydrofuran were added to the resultant. Stirring was sequentially performed for two hours. After that, when the reaction solution was checked with TLC, it was found that the intermediate compound (a) completely disappeared, and an odor of 3-mercaptopropanol also disappeared. 6.59 g (65.1 mmol) of triethylamine (Et₃N) were added and cooled to a temperature of 0 degrees Celsius. 5.45 g (52.1 mmol) of methacryloyl chloride were slowly dropped to the resultant. Stirring was sequentially performed for two hours. After that, 35 mL of a 2N sodium hydroxide aqueous solution were added to the reaction solution. The resultant was separated into an organic layer and a water layer by a separating funnel, and then the water layer was extracted twice by 20 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees of Celsius. Thus, 13.04 g of a crude product of a light yellow liquid containing the intermediate compound (c) as a main component was obtained.

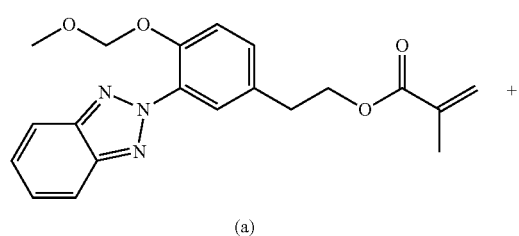

(a)

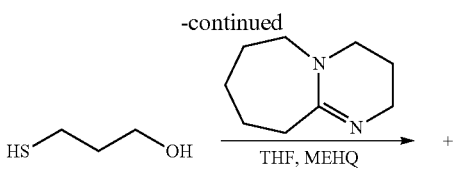

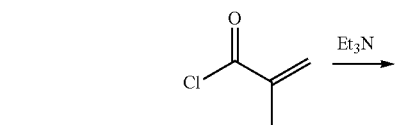

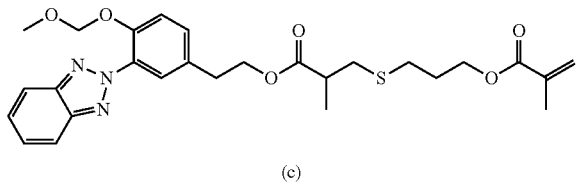

(c)

Synthesis of Compound (1B)

13.04 g of a crude product containing the intermediate compound (c) as a main component and 90 mL of tetrahydrofuran (dehydration) were measured and put in a 200 milliliter-reactor vessel, and the resultant was stirred to obtain a uniform solution. 10 mL of 12N hydrochloric acid were slowly dropped to the resultant. Stirring was sequentially performed all night. After that, when the reaction solution was checked with TLC, it was found that the intermediate compound (c) completely disappeared. The resultant was replaced in a separating funnel, and was washed three times with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees Celsius. 2 mL of a chloroform solution with 1 mg/ml of MEHQ were added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a compound (1B) was obtained. The yield amount was 6.00 g (12.4 mmol), and the yield from the intermediate compound (a) to the compound (1B) through the intermediate compound (c) was 47.6%.

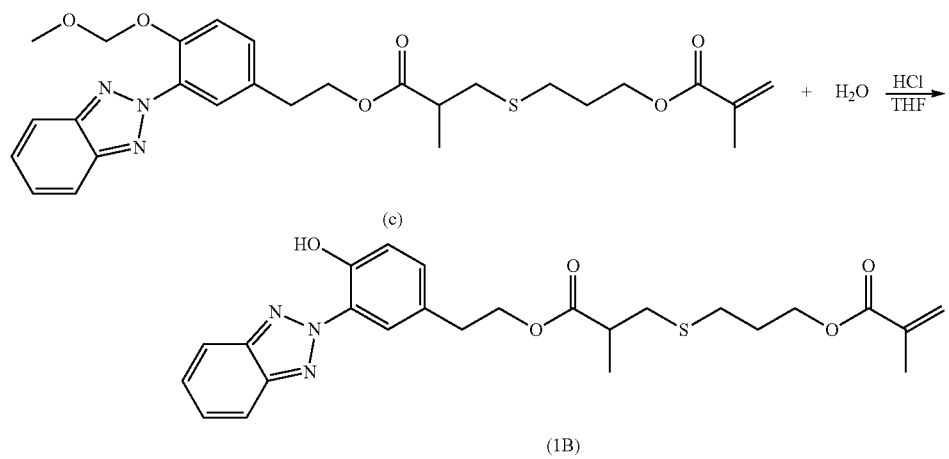

(1B)

Measurement results of 1H-NMR being the compound (1B) are shown below.

$^1$H-NMR (500 MHz, DMSO-d6): δ1.10-1.11 (3H, d), 1.76-1.82 (2H, q), 1.85 (3H, s), 2.48-2.72 (5H, m), 2.93-2.95 (2H, t), 4.08-4.10 (2H, t), 4.27-4.29 (2H, t), 5.64 (1H, s), 6.00 (1H, s), 7.11-7.12 (1H, d), 7.32-7.34 (1H, dd), 7.53-7.55 (2H, m), 7.77-7.78 (1H, d), 8.02-8.04 (2H, m), 10.46 (1H, s)

Example 3 (Synthesis of Compound (1C))

Synthesis of Intermediate Compound (d)

The intermediate compound (a) described in Example 1 was used, and thus an intermediate compound (d) was synthesized. 9.70 g (26.4 mmol) of the intermediate compound (a), 194 mg (1.56 mmol) of MEHQ, and 30 mL of tetrahydrofuran (dehydration) were measured and put in a 300 milliliter-reactor vessel, and the resultant was stirred to obtain a uniform solution. A dilute solution of 2.80 g (26.4 mmol) of 3-melcapto-2-butanol and 0.201 g (1.32 mmol) of 1,8-diazabicyclo [5.4.0]-7-undecene with 5 mL of tetrahydrofuran were added to the resultant. Stirring was sequentially performed for three days. After that, when the reaction solution was checked with TLC, it was found that the intermediate compound (a) completely disappeared, and an odor of 3-mercapto-2-butanol also disappeared. 6.68 g (66.0 mmol) of triethylamine (Et$_3$N) were added and cooled to a temperature of 0 degrees Celsius. 5.52 g (52.8 mmol) of methacryloyl chloride were slowly dropped to the resultant. Stirring was sequentially performed for two hours. After that, 35 mL of a 2N sodium hydroxide aqueous solution were added to the reaction solution. The resultant was separated into an organic layer and a water layer by a separating funnel, and then the water layer was extracted twice by 20 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees of Celsius. Thus, 15.35 g of a crude product of a light yellow liquid containing the intermediate compound (d) as a main component was obtained.

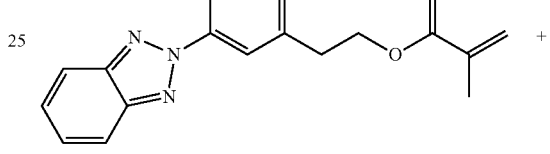

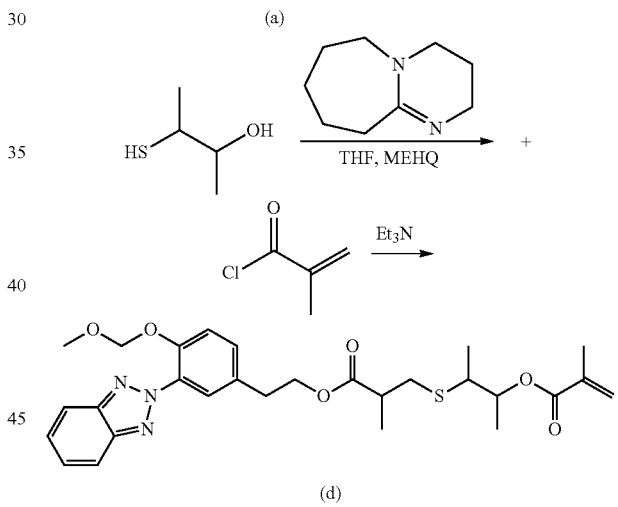

Synthesis of Compound (1C)

15.35 g of a crude product containing the intermediate compound (d) as a main component and 90 mL of tetrahydrofuran (dehydration) were measured and put in a 200 milliliter-reactor vessel, and the resultant was stirred to obtain a uniform solution. 10 mL of 12N hydrochloric acid were slowly dropped to the resultant. Stirring was sequentially performed all night. After that, when the reaction solution was checked with TLC, it was found that the intermediate compound (d) completely disappeared. The resultant was replaced in a separating funnel, and was washed three times with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees Celsius. 2 mL of a chloroform solution with 1 mg/mL of MEHQ was added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a compound (1C) was obtained. The yield amount was 8.21 g (16.5 mmol), and the yield from the intermediate compound (a) to the compound (1C) through the intermediate compound (d) was 62.5%.

into an organic layer and a water layer by a separating funnel, and then the water layer was extracted twice by 20 mL of ethyl acetate. The organic layer and the extracted layer were collectively washed twice with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees of Celsius. Thus, 20.95 g of a crude product of a yellow liquid containing the intermediate compound (e) as a main component was obtained.

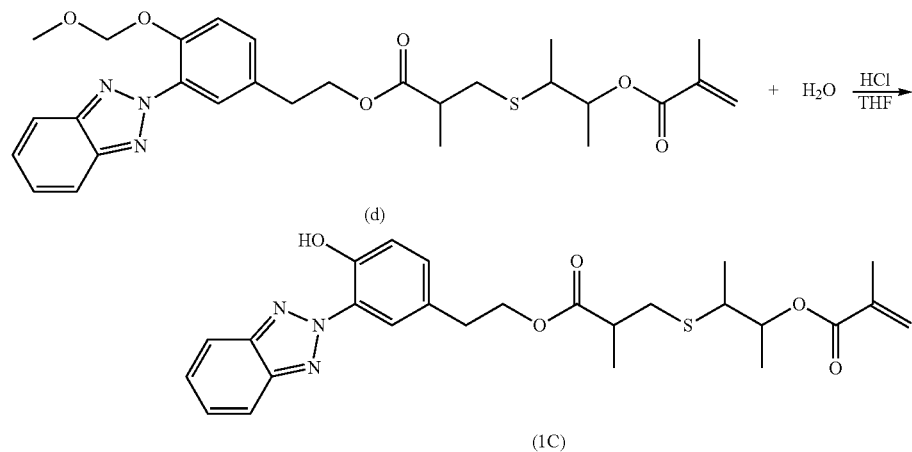

Measurement results of 1H-NMR being the compound (1C) are shown below.

$^1$H-NMR (500 MHz, DMSO-d6): δ1.08-1.19 (9H, m), 1.85 (3H, s), 2.58-2.68 (2H, m), 2.72-2.81 (1H, m), 2.86-2.95 (3H, m), 4.14-4.17 (2H, t), 4.26-4.30 (2H, t), 4.88-4.94 (1H, m), 5.64 (1H, s), 5.99 (1H, s), 7.11-7.12 (1H, d), 7.32-7.34 (1H, dd), 7.53-7.56 (2H, m), 7.77-7.78 (1H, d), 8.02-8.05 (2H, m), 10.47 (1H, s)

Example 4 (Synthesis of Compound (1D))

The intermediate compound (a) described in Example 1 was used, and thus an intermediate compound (e) was synthesized. 9.67 g (26.3 mmol) of the intermediate compound (a), 193 mg (1.55 mmol) of MEHQ, and 30 mL of tetrahydrofuran (dehydration) were measured and put in a 300 milliliter-reactor vessel, and the resultant was stirred to obtain a uniform solution. A dilute solution of 2.85 g (26.3 mmol) of α-thioglycerol and 0.200 g (1.32 mmol) of 1,8-diazabicyclo [5.4.0]-7-undecene with 5 mL of tetrahydrofuran were added to the resultant. Stirring was sequentially performed for two hours. After that, when the reaction solution was checked with TLC, it was found that the intermediate compound (a) completely disappeared, and an odor of α-thioglycerol also disappeared. 11.99 g (118.4 mmol) of triethylamine (Et₃N) were added and cooled to a temperature of 0 degrees Celsius. 11.01 g (105.3 mmol) of methacryloyl chloride were slowly dropped to the resultant. Stirring was sequentially performed for two hours, and stirring was then performed all night at a room temperature. 35 mL of a 2N sodium hydroxide aqueous solution were added to the reaction solution. The resultant was separated

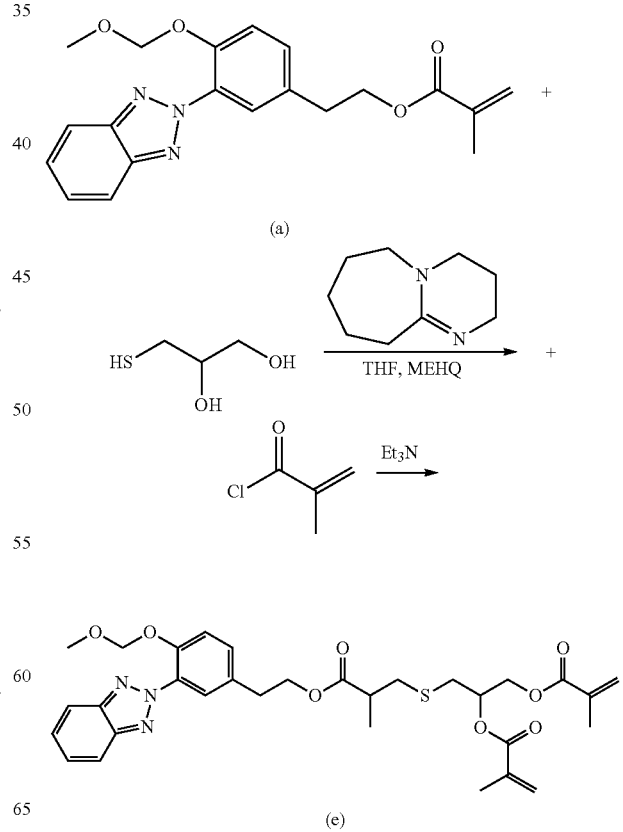

Synthesis of Compound (1D)

20.95 g of a crude product containing the intermediate compound (e) as a main component and 90 mL of tetrahydrofuran (dehydration) were measured and put in a 200 milliliter-reactor vessel, and the resultant was stirred to obtain a uniform solution. 10 mL of 12N hydrochloric acid were slowly dropped to the resultant. Stirring was sequentially performed all night. After that, when the reaction solution was checked with TLC, it was found that the intermediate compound (e) completely disappeared. The resultant was replaced in a separating funnel, and was washed three times with 50 mL of a saturated saline solution. The resultant was replaced in a vessel, and anhydrous magnesium sulfate was added.

Solid matters were removed through filtration, and the filtrate was concentrated under a low pressure at a temperature of 40 degrees Celsius. 2 mL of a chloroform solution with 1 mg/mL of MEHQ was added to the slightly yellow-colored liquid obtained through refining with a silica gel column (a development solvent satisfied n-hexane:ethyl acetate=3:1), and the resultant was dried under a low pressure at a temperature of 40 degrees Celsius for three hours. Thus, a compound (1D) was obtained. The yield amount was 8.32 g (14.7 mmol), and the yield from the intermediate compound (a) to the compound (1D) through the intermediate compound (e) was 55.7%.

F-line (having a wavelength of 486.1 nm), and a g-line (having a wavelength of 435.8 nm). Further, a $\theta_{g,F}$ value and a $v_d$ value were calculated from the expressions given below.

$$\theta_{g,F} = (n_g - n_F)/(n_F - n_C)$$

$$v_d = (n_d - 1)/(n_F - n_C)$$

Note that, among the acquired compounds, the crystallized compound (1A) was heated to be melted into a liquid state, and then cooled to a measurement temperature, and a refractive index was measured in a supersaturated liquid state. The compound (1B), the compound (1C), and the compound (1D) were obtained as a liquid compound, and thus a refractive index was measured in a liquid state as it is at a room temperature. Results are shown in Table 1.

TABLE 1

| | EXAMPLE 1 (COMPOUND (1A)) | EXAMPLE 2 (COMPOUND (1B)) | EXAMPLE 3 (COMPOUND (1C)) | EXAMPLE 4 (COMPOUND (1D)) |
|---|---|---|---|---|
| $n_C$ | 1.5918 | 1.5841 | 1.5763 | 1.5713 |
| $n_d$ | 1.6007 | 1.5924 | 1.5847 | 1.5797 |
| $n_F$ | 1.6262 | 1.6172 | 1.6083 | 1.6021 |
| $n_g$ | 1.6538 | 1.6438 | 1.6340 | 1.6268 |
| $\theta_{g,F}$ | 0.802 | 0.804 | 0.803 | 0.802 |
| $v_d$ | 17.5 | 17.9 | 18.3 | 18.8 |

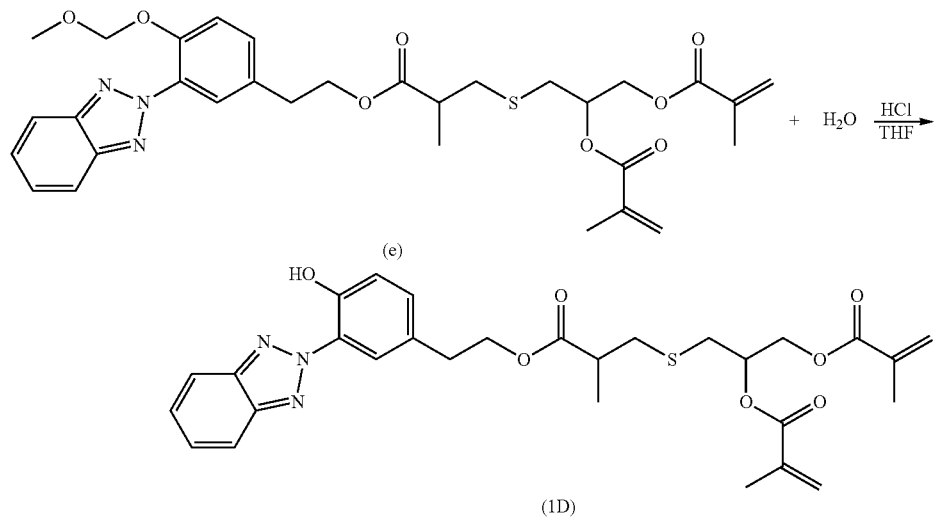

(e)

(1D)

Measurement results of 1H-NMR being the compound (1D) are shown below.

$^1$H-NMR (500 MHZ, DMSO-d6): δ1.09-1.11 (3H, dd), 1.84 (6H, s), 2.61-2.85 (5H, m), 2.93-2.95 (2H, t), 4.20-4.24 (1H, dd), 4.25-4.30 (2H, q), 4.35-4.39 (1H, m), 5.14-5.20 (1H, m), 5.66 (1H, s), 5.67 (1H, s), 5.98 (1H, s), 5.99 (1H, s), 7.11-7.12 (1H, d), 7.32-7.34 (1H, dd), 7.52-7.56 (2H, m), 7.77-7.78 (1H, d), 8.02-8.05 (2H, m), 10.46 (1H, s)

<Physical Property Evaluation of Compound>

Measurement and Evaluation

A refractive index of a compound was measured by using a multi-wavelength refractometer (manufactured by Anton Paar Japan). Refractive indexes $n_C$, $n_d$, $n_F$, and $n_g$ were measured respectively for a C-line (having a wavelength of 656.3 nm), a d-line (having a wavelength of 587.6 nm), an II. Production of Resin Precursor and Physical Property Evaluation (Production of Main Agent 3)

First, a main agent 3 (a compound represented by Formula (iii)) described later was produced in accordance with the following method.

First, in an argon gas flow, 10.00 g (55.6 mmol) of 3-formyl-4-methoxyphenylboronic acid, 50 mL of tetrahydrofuran (THF, dehydration), and 50 mL of ethanol (dehydration) were measured and put in a 300 milliliter-reactor vessel, and the resultant was stirred at a temperature of 0 degrees Celsius. 1.36 g (36.0 mmol) of sodium borohydride (NaBH$_4$) were added to the resultant by a small amount each. After stirring at a temperature of 0 degrees Celsius for two hours, the reaction check was performed with TLC, and disappearance of the raw materials was confirmed. Immediately after 50 mL of city water were added to the resultant to stop the reaction, white precipitate was generated promptly.

Subsequently, the suspension was subjected to filtration under a low pressure, and an organic solvent was removed. Hydrochloric acid having a concentration of 2 mol/L was added until the suspension became neutral. After that, the precipitate was recovered through filtration. The recovered matters through filtration were washed with 50 mL of ethyl acetate, and were dried under a low pressure at a temperature of 40 degrees Celsius. Thus, as the recovered matters, an intermediate compound (iii-1) ((3-hydroxymethyl)-4-methoxy-phenyl) boronic acid) was obtained. The yield amount was 9.27 g (50.9 mmol), and the yield was 91.5%.

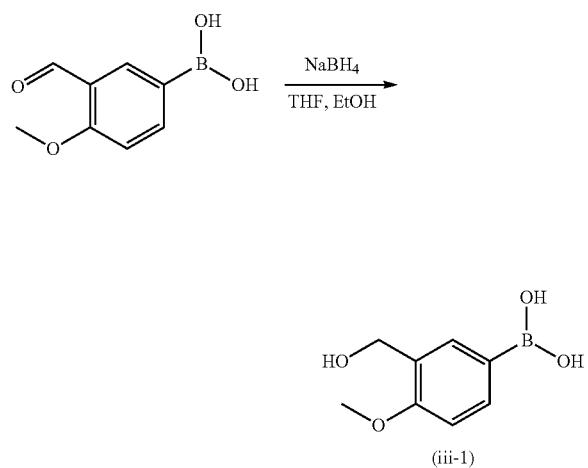

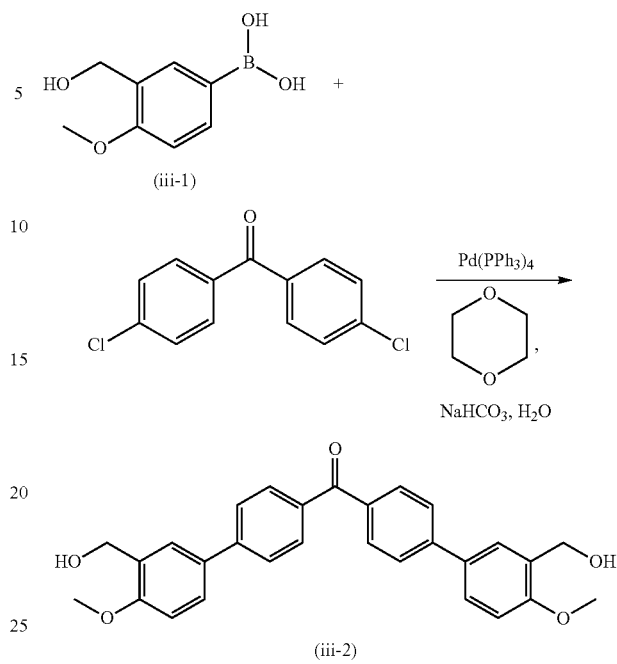

Subsequently, 3.30 g (12.5 mmol) of 4,4'-dichlorobenzophenone, 5.00 g (27.5 mmol) of the intermediate compound (iii-1), 3.57 g (42.5 mmol) of sodium hydrogen carbonate, 150 mL of 1,4-dioxane, and 75 mL of distilled water were measured and put in a 500 milliliter-reactor vessel, and the resultant was subjected to argon bubbling while being stirred at a room temperature. After stirred for 30 minutes, 0.29 g (0.25 mmol) of tetrakis(triphenylphosphine)palladium (Pd (Ph$_3$)$_4$) were added to the reaction system. Further, argon bubbling was switched to an argon gas flow, and stirring was performed at a temperature of 90 degrees Celsius over one night. After that, the reaction check was performed with TLC, disappearance of the raw materials was confirmed, and then heating was stopped. After the reaction solution was left and cooled to a room temperature, 25 mL of a saturated ammonium chloride aqueous solution and 150 mL of city water were added, and the resultant was stirred for 30 minutes. The deposited precipitate was recovered through filtration, was washed with 300 mL of water, and thus yellowish-white powder was obtained.

The obtained yellowish-white powder was dried under a low pressure at a temperature of 70 degrees Celsius over one night. 900 mL of a mixed solution in which tetrahydrofuran:chloroform=1:9 was satisfied were added to the powder, and the resultant was heated at a temperature of 60 degrees Celsius. The solution was refined with a silica gel column (a development solvent satisfied tetrahydrofuran:chloroform=1:9), and thus an intermediate compound (iii-2) was obtained. The yield amount was 4.86 g (10.7 mmol), and the yield was 85.6%.

Further, in an argon gas flow, 2 g (4.40 mmol) of the intermediate compound (iii-2) and 80 mL of dichloromethane (dehydration) were measured and put in a 200 milliliter-reactor vessel, and the resultant was cooled to a temperature of 0 degrees Celsius. 1.01 g (3.74 mmol) of phosphorus tribromide (PBr$_3$) were dropped to the resultant for five minutes, and a temperature thereof was increased to a room temperature. After stirring for three hours, the reaction check was performed with TLC and the HPLC analysis, disappearance of the raw materials was confirmed, and then stirring was stopped. 80 mL of city water at a temperature of 10 degrees Celsius or below were added to the resultant, and stirred was performed again for 30 minutes. Further, after the deposited precipitate was recovered through filtration, the filtrate was separated into an organic layer and a water layer. The water layer was washed twice with 50 mL of dichloromethane, and thus an organic component dissolved in the water layer was recovered. Subsequently, the organic layer and the organic components recovered from the water layer were mixed to be a mixed solution. The mixed solution was subjected to sucking filtration. Note that, at the time of sucking filtration, the water was frozen, which stopped filtration, and hence an operation was carried out while warming the water from above the funnel.

After the obtained filtrate was concentrated under a low pressure, the recovered matters through filtration were added again, and 50 mL of tetrahydrofuran were added to the resultant for suspension. With this, the suspension was obtained. 200 mL of city water were added to the obtained suspension, and the deposited precipitate was recovered through filtration. Regarding the filtrate, after washing with city water until the filtrate became neutral, washing with 20 mL of methanol was further performed. The obtained white powder was dried under a low pressure at a temperature of 70 degrees Celsius over one night. Thus, an intermediate compound (iii-3) was obtained. The yield amount was 2.36 g (4.07 mmol), and the yield was 92.5%.

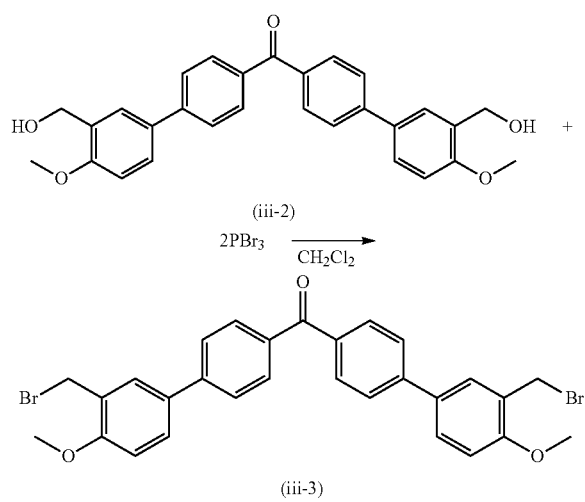

(iii-2)

2PBr₃ / CH₂Cl₂ →

(iii-3)

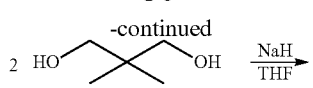

(iii-4)

In an argon gas flow, 25 mL of tetrahydrofuran (dehydration) and 0.47 g (11.7 mmol) of sodium hydride (concentration of 60%) were measured and put in a 100 milliliter-reactor vessel, and the resultant was cooled at a temperature of 0 degrees Celsius. A dilute solution of 2.98 g (28.6 mmol) of 2,2-dimethyl-1,3-propanediol with 5 mL of tetrahydrofuran were slowly dropped to the resultant for 15 minutes, and a temperature thereof was increased to a room temperature. After stirring for an hour, 1.6 g of the intermediate compound (iii-3) were added at once, and the resultant was stirred at a temperature of 60 degrees Celsius for 16 hours. After that, the reaction check was performed with TLC and the HPLC analysis, disappearance of the raw materials was confirmed. 30 mL of city water were added to the resultant, and the reaction was stopped. Subsequently, separation into an organic layer and a water layer was performed by adding 100 mL of ethyl acetate to the reaction solution. The water layer was washed twice with 30 mL of ethyl acetate, and thus an organic component dissolved in the water layer was recovered. Further, the organic layer and the organic components recovered from the water layer were mixed to be a mixed solution. The obtained mixed solution was washed subsequently with water and a saturated saline solution, and then was dried with magnesium sulfate.

Subsequently, the dried mixed solution was concentrated under a low pressure, and the solvent was distillated. With this, 4.21 g of yellowish solid matters were obtained. The resultant was refined with a silica gel column (a development solvent satisfied ethyl acetate:chloroform=1:4), and the intermediate compound (iii-4) being white solid matters was obtained. The obtained white solid matters were dried under a low pressure at a temperature of 70 degrees Celsius for an hour. The yield amount was 1.54 g (2.46 mmol), and the yield was 71.3%.

(iii-3)

In an argon gas flow, 1.50 g (2.39 mmol) of the intermediate compound (iii-4), 12 mL of chloroform (dehydration), 2.30 g (22.7 mmol) of triethylamine (TEA), and 6.0 mg (48 μmol) of p-methoxyphenol were measured and put in a 30 milliliter-reactor vessel, and the resultant was cooled at a temperature of 0 degrees Celsius. When 0.85 g (8.13 mmol) of methacryloylchloride were dropped to the resultant for five minutes, the solution color was changed to pink, and triethylaminehydrochloride was disposed. Subsequently, a temperature was increased from 0 degrees Celsius to a room temperature, and stirring was performed for an hour. After that, the reaction check was performed with TLC and the HPLC analysis, and disappearance of the raw materials was confirmed. 6 mL of city water were added to the resultant, and the reaction was stopped. Subsequently, the reaction solution was separated into an organic layer and a water layer. The water layer was washed twice with 30 mL of chloroform, and thus an organic component dissolved in the water layer was recovered. Further, the organic layer and the organic components recovered from the water layer were mixed to be a mixed solution. The mixed solution was washed subsequently with water and a saturated saline solution, and then was dried with sodium sulfate.

Subsequently, 6.0 mg (48 μmol) of p-methoxyphenol and 10 mL of toluene were added in a dried mixed solution. Further, the mixed solution was concentrated under a low pressure, and triethylamine and the solvent were distillated. With this, 2.80 g of a crude matter were obtained. The obtained crude matter was refined with a silica gel column (a development solvent was chloroform).

Further, a chloroform solution with 0.9 mg (corresponding to 500 ppm) of p-methoxyphenol was added to the fraction of the silica gel column obtained in the previous step, the resultant was concentrated under a low pressure at a temperature of 30 degrees Celsius or below, and thus yellow and white solid matters (main agent 3 (compound (iii))) being a target object were obtained. In the concentration step, the resultant was not held under a low pressure for a long time in order to prevent polymerization. The yield amount was 1.73 g (2.27 mmol), and the yield was 94.9%. The melting point was at a temperature of 100 degrees Celsius.

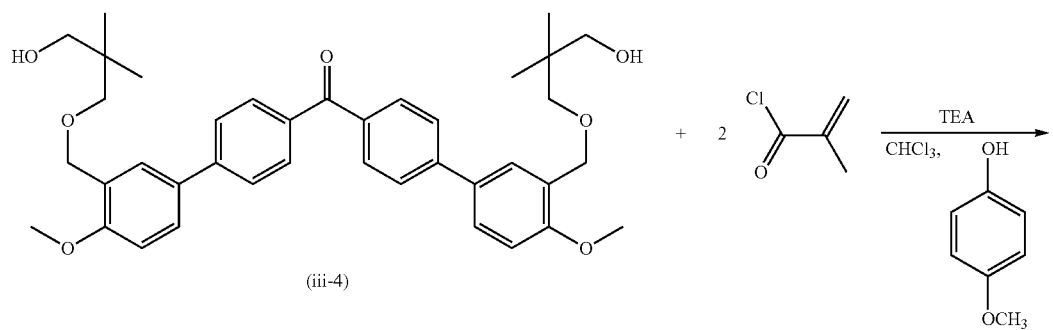

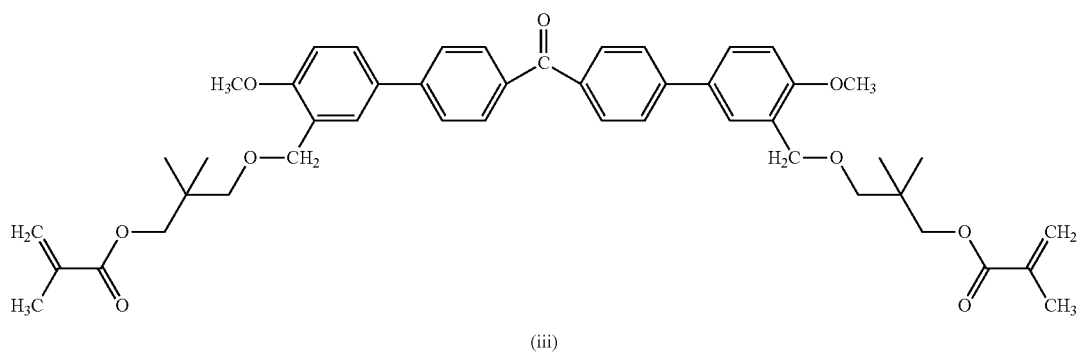

Measurement results of $^1$H-NMR being the main agent 3 (the compound (iii)) are shown below.

$^1$H-NMR (300 MHz, DMSO-d6): δ0.95 (12H, s), 1.81 and 1.85 (6H, s), 3.31 (4H, s), 3.84 (6H, s), 3.94 (4H, s), 4.54 (4H, s), 5.59 and 5.97 (4H, s), 7.11-7.14 (2H, d), 7.69-7.86 (12H, m)

m.p.=100 degrees Celsius

Examples 5 to 8

The compound (1A) and other component were mixed at a ratio shown in Table 2, and resin precursors (1A-1) to (1A-4) were produced. Then, a state under an ordinary temperature and pressure was confirmed for each of the obtained resin precursors. Note that a ratio of combination in the table is based on mass % unless otherwise specified.

A component used for each of the resin precursors is indicated.

-Main Agent 1

9,9-bis [4-(2-acryloyloxyethoxy)phenyl]fluorene (Formula (i))

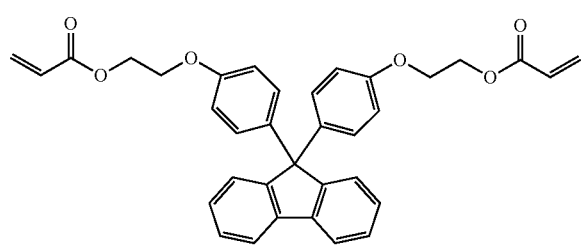

-Main Agent 2
1,6-diacryloyloxy-2,2,3,3,4,4,5,5-octafluorohexane (Formula (ii))

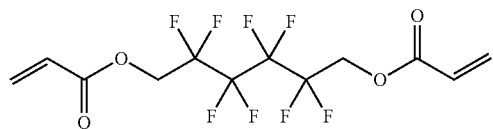

(ii)

-Main Agent 3
The compound represented by Formula (iii) given below (Formula (iii))

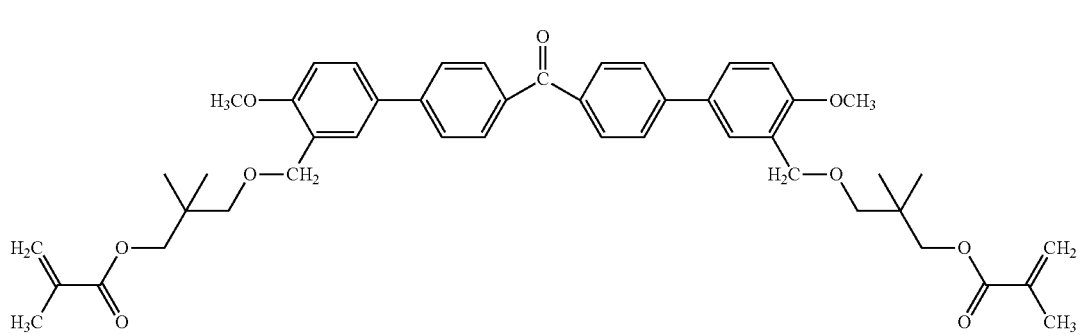

(iii)

-Compatibility Accelerator:
methoxytrypropyleneglycolacrylate (Formula (iv))

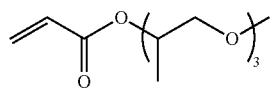

(iv)

-Photopolymerization Initiator 1:
1-hydroxy-cyclohexyl-phenyl-ketone (Formula (v))

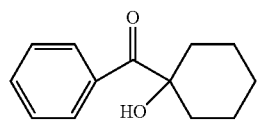

(v)

-Photopolymerization Initiator 2:
bis(2-4-6-trimethylbenzoyl)-phenylphosphineoxide (Formula (vi))

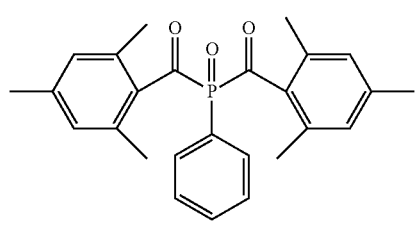

(vi)

-Radical Scavenger:
bis(1,2,2,6,6-pentamethyl-4-piperidyl) sebacate (Formula (vii))+methyl1,2,2,6,6-pentamethyl-4-piperidylsebacate (Formula (viii))

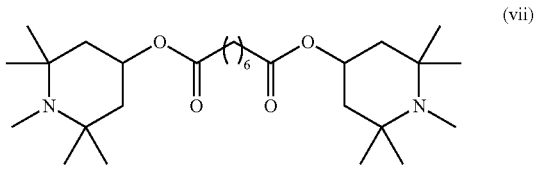

(vii)

-continued

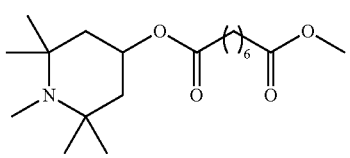

(viii)

-Ultraviolet Light Absorber:
2-(2-hydroxy-5-tert-octylphenyl)-2H-benzotriazole (Formula (ix))

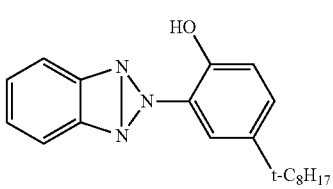

(ix)

<Physical Property Evaluation of Resin Precursor>
(Production of Sample for Refractive Index Measurement)

A physical property of each resin precursor was measured in a liquid state without curing.

Measurement and Evaluation

Similarly to the method of measuring a physical property of the compound, refractive indexes $n_C$, $n_d$, $n_F$, and $n_g$ were measured for each resin precursor, and a $\theta_{g,F}$ value and a $v_d$ value were calculated. Results are shown in Table 2.

[Table 2]

TABLE 2

|  | EXAMPLE 5 | EXAMPLE 6 | EXAMPLE 7 | EXAMPLE 8 |
|---|---|---|---|---|
| RESIN PRECURSOR NAME | 1A-1 | 1A-2 | 1A-3 | 1A-4 |
| COMPOUND (1A) | 50 | 33.34 | 25 | 40 |
| MAIN AGENT 1 (COMPOUND (i)) | 19 | 25.34 | 28.5 | 15.2 |
| MAIN AGENT 2 (COMPOUND (ii)) | 25.9 | 34.53 | 38.85 | 20.72 |
| MAIN AGENT 3 (COMPOUND (iii)) |  |  |  | 20 |
| COMPATIBILITY ACCELERATOR (COMPOUND (iv)) | 2 | 2.67 | 3 | 1.6 |
| PHOTOPOLYMERIZATION INITIATOR 1 (COMPOUND (v)) | 1 | 1.33 | 1.5 | 0.8 |
| PHOTOPOLYMERIZATION INITIATOR 2 (COMPOUND (vi)) | 0.1 | 0.13 | 0.15 | 0.08 |
| RADICAL SCAVENGER (COMPOUND (vii) + (viii)) | 1 | 1.33 | 1.5 | 0.8 |
| ULTRAVIOLET LIGHT ABSORBER (COMPOUND (ix)) | 1 | 1.33 | 1.5 | 0.8 |
| TOTAL (MASS %) | 100 | 100 | 100 | 100 |
| STATE UNDER ORDINARY TEMPERATURE AND PRESSURE | LIQUID STATE | LIQUID STATE | LIQUID STATE | LIQUID STATE |
| $n_c$ | 1.5453 | 1.5314 | 1.5220 | 1.5566 |
| $n_d$ | 1.5524 | 1.5370 | 1.5276 | 1.5643 |
| $n_F$ | 1.5709 | 1.5541 | 1.5432 | 1.5842 |
| $n_g$ | 1.5903 | 1.5708 | 1.5585 | 1.6055 |
| $\theta_{g,F}$ | 0.758 | 0.736 | 0.722 | 0.772 |
| $v_d$ | 21.6 | 23.7 | 24.9 | 20.4 |

III. Production of Cured Object and Physical Property Evaluation

Examples 9 to 12

Each of the resin precursors (1A-1) to (1A-4) was sandwiched between synthetic quarts (t=1 mm), was irradiated with light from a high luminance mercury xenon lamp ("LC8" manufactured by Hamamatsu Photonics) through a filter cutting a wavelength under 385 nm to be cured. With this, cured objects (1A-1) to (1A-4) were obtained. A state under an ordinary temperature and pressure was confirmed for each cured object.

<Physical Property Evaluation of Cured Object>
(Production of Sample for Refractive Index Measurement)

A silicone rubber sheet having a rectangular opening was placed on a quartz glass substrate, and the opening was filled with a resin precursor and then closed with a quartz glass substrate. Subsequently, the resin precursor was irradiated with ultraviolet light through the quartz glass substrate to be cured. Further, the cured object was released, and a sample for refractive index measurement, which had a shape of 15 mm×15 mm and a thickness of 0.5 mm, was obtained.

Measurement and Evaluation

Similarly to the method of measuring a physical property of the compound, refractive indexes $n_C$, $n_d$, $n_F$, and $n_g$ were measured, and a $\theta_{g,F}$ value and an abbe number ($v_d$ value) were calculated. Results are shown in Table 3.

[Table 3]

TABLE 3

|  | EXAMPLE 9 | EXAMPLE 10 | EXAMPLE 11 | EXAMPLE 12 |
|---|---|---|---|---|
| USED RESIN PRECURSOR NAME | 1A-1 | 1A-2 | 1A-3 | 1A-4 |
| CURED OBJECT NAME | 1A-1 | 1A-2 | 1A-3 | 1A-4 |
| $n_c$ | 1.5706 | 1.5550 | 1.5461 | 1.5800 |
| $n_d$ | 1.5775 | 1.5614 | 1.5524 | 1.5875 |
| $n_F$ | 1.5964 | 1.5777 | 1.5670 | 1.6083 |
| $n_g$ | 1.6160 | 1.5945 | 1.5822 | 1.6302 |
| $\theta_{g,F}$ | 0.760 | 0.740 | 0.727 | 0.774 |
| $v_d$ | 22.4 | 24.7 | 26.4 | 20.8 |

It was confirmed from above that the compound and the cured object obtained from the resin precursor containing the compound in each example had a high $\theta_{g,F}$ value and a low dispersion characteristic of a refractive index ($v_d$ value).

Examples 13 to 16

Further, for each cured object shown in Table 4, an inner transmittance 27 days after curing and a wavelength at which the inner transmittance was 80% were measured.
(Production of Sample for Transmittance Measurement)

Similarly to the method of producing a sample for refractive index measurement, which is described above, a sample having a thickness of 0.5 mm and a sample having a thickness of 1.0 mm were produced as samples for transmittance measurement for each cured object. Further, the resin precursors that were left to stand for 27 days after curing were used for measurement.
(Evaluation of Inner Transmittance)

A transmittance was measured for the sample having a thickness of 0.5 mm and the sample having a thickness of 1.0 mm, and was corrected in the expression given below. For measurement, a spectrophotometer ("UV-4700" manufactured by Shimadzu Corporation) was used.

Inner transmittance (%)=$(A/B)^{[100/(a-b)]} \times 100$

A: Transmittance with a thickness of 1.0 mm
B: Transmittance with a thickness of 0.5 mm
a: Actually measured dimension of a sample having a plate thickness of 1.0 mm
b: Actually measured dimension of a sample having a plate thickness of 0.5 mm
Inner transmittance conversion data for 0.5 mm
(Wavelength ($\lambda_{80}$) at which Inner Transmittance was 80%)

First, a sample having a thickness of 12 mm and a sample having a thickness of 2 mm, which were subjected to parallel polishing, were prepared. An inner transmittance was measured in a wavelength range from 200 to 700 nm when light parallel to the thickness direction was incident, and was converted to an inner transmittance for a thickness of 10 mm. Further, a wavelength at which an inner transmittance was 80% was measured as $\lambda_{80}$.

Results indicating an inner transmittance (%) at each wavelength and a wavelength (Ago; unit nm) at which an inner transmittance was 80% in Examples 13 to 16 are shown in Table 4.

[Table 4]

TABLE 4

|  | EXAMPLE 13 | EXAMPLE 14 | EXAMPLE 15 | EXAMPLE 16 |
| --- | --- | --- | --- | --- |
| CURED OBJECT NAME | 1A-1 | 1A-2 | 1A-3 | 1A-4 |
| 420 nm | 92% | 95% | 96% | 89% |
| 440 nm | 99% | 99% | 99% | 99% |
| 460 nm | 99% | 99% | 99% | 99% |
| 480 nm | 99% | 99% | 99% | 99% |
| 500 nm | 99% | 99% | 99% | 99% |
| 550 nm | 100% | 100% | 100% | 100% |
| 600 nm | 100% | 100% | 100% | 100% |
| 650 nm | 100% | 100% | 100% | 100% |
| $\lambda_{80}$ | 415 nm | 412 nm | 410 nm | 416 nm |

[Formula 2]

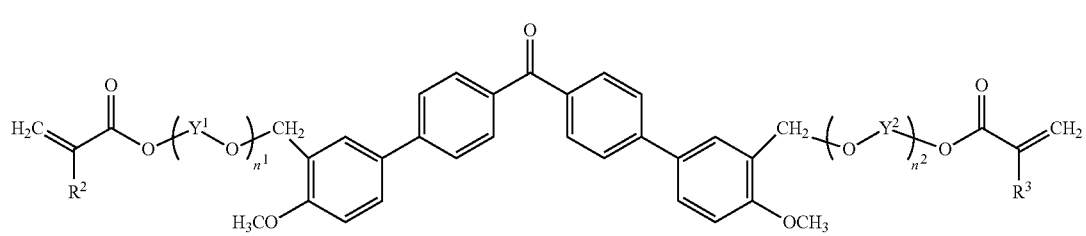

(2)

<Light Resistance Test>

A cured object (1A-1) after curing was stable and a cured object (1A-1) after a light resistance test were used as samples. Specifically, the test was performed by the following procedure. First, the samples were sticked on a jig, were loaded in a chamber of an ultraviolet fade meter ("U48 type" manufactured by Suga Test Instruments Co., Ltd.), and were irradiated with ultraviolet light generated by arc discharge between two ultraviolet carbons ("UVL-C" and "UVL-S") for a total of 144 hours (48 hours×3). Then, a degree of light resistance was checked based on a change in spectral transmittance of each of the samples before and after the test. Note that the test was performed at a room temperature. Results are illustrated in FIG. 6.

Figure 6:
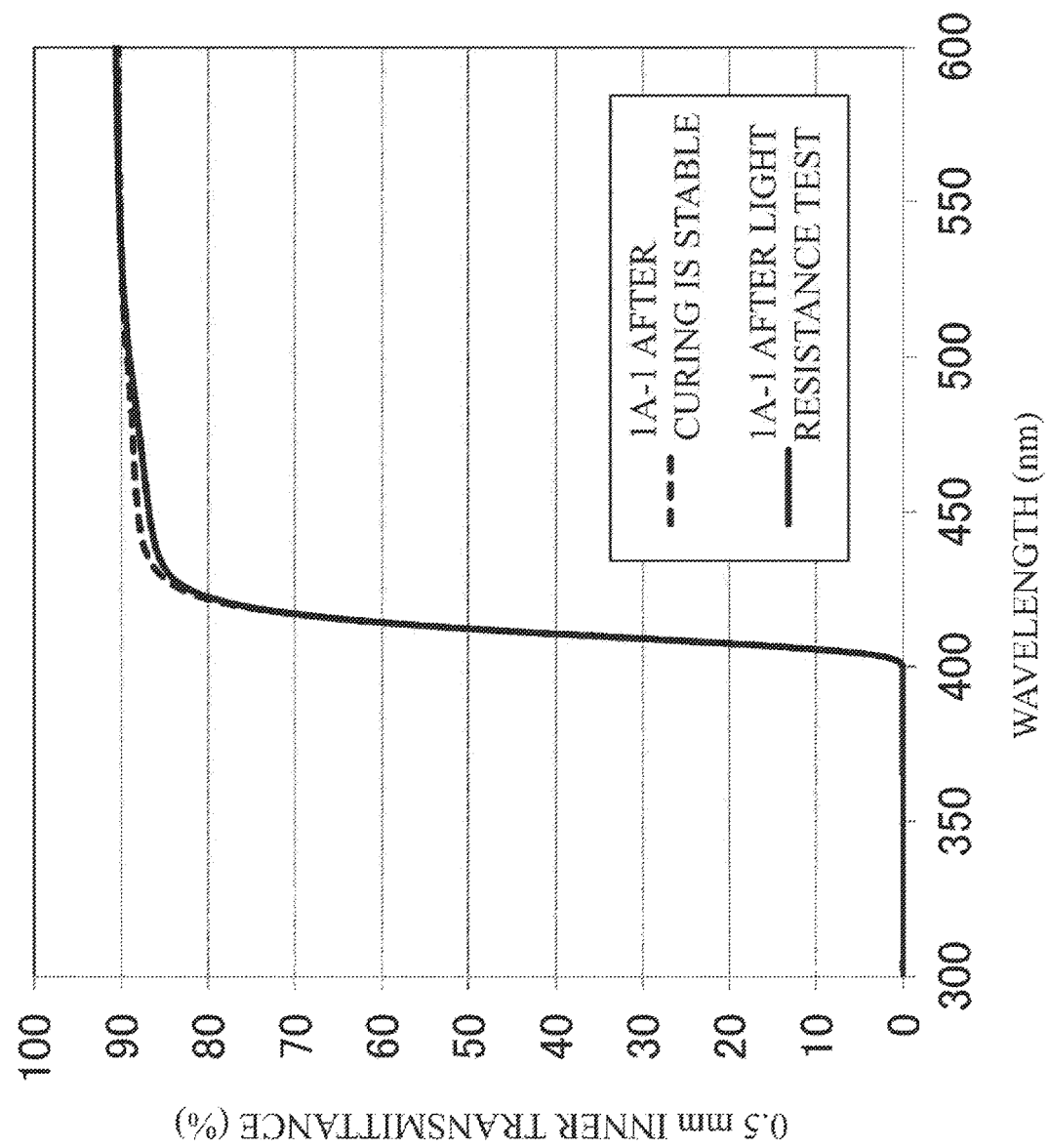
FIG. 6 is a graph illustrating a result of a light resistance test in an example.

As illustrated in FIG. 6, it was at least confirmed that light resistance was also excellent in the present example.

The invention claimed is:

1. A compound represented by Formula (1) given below

[Formula 1]

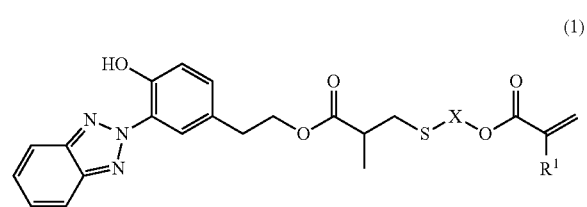

(1)

wherein in the formula, $R^1$ represents a hydrogen atom or a methyl group, and X represents a $C_{2\ to\ 6}$ alkylene group, a $C_{4\ to\ 6}$ alkylene group containing an oxygen atom and/or a sulfur atom, or a $C_{3\ to\ 6}$ alkylene group in which at least one hydrogen is replaced with an acryloxy group or a methacryloxy group.

2. A resin precursor containing the compound according to claim 1 and a curable composition.

3. The resin precursor according to claim 2, wherein the curable composition is a photocurable composition.

4. The resin precursor according to claim 2, wherein the curable composition includes one or more compounds selected from a group consisting of a compound represented by Formula (2) given below, a fluorine-containing acrylate compound, a fluorine-containing methacrylate compound, an acrylate compound having a fluorene structure, a methacrylate compound having a fluorene structure, a diacrylate compound, and a dimethacrylate compound wherein in the formula, $R^2$ and $R^3$ independently represent a hydrogen atom or a methyl group, $Y^1$ and $Y^2$ independently represent a $C_{1\ to\ 9}$ alkylene group, and $n^1$ and $n^2$ independently represent an integer from 0 to 3.

5. The resin precursor according to claim 2, wherein the curable composition includes one or more compound selected from a group consisting of 1,6-diacryloyloxy-2,2,3,3,4,4,5,5-octafluorohexane, 1,6-dimethacryloyloxy-2,2,3,3,4,4,5,5-octafluorohexane, 9,9-bis [4-(2-acryloyloxyethoxy)phenyl]fluorene, and 1,6-hexanediol diacrylate.

6. The resin precursor according to claim 2, wherein a content ratio of the compound represented by Formula (1) is 10 to 90 mass %.

7. A cured object obtained by curing the resin precursor according to claim 2.

8. The cured object according to claim 7, wherein a $\theta_{g,F}$ value is 0.5 or greater.

9. The cured object according to claim 7, wherein a refractive index ($n_d$) with respect to a d-line is 1.50 or greater and 1.65 or less.

10. The cured object according to claim 7, wherein an abbe number ($v_d$) is 10 or greater and 40 or less.

11. The cured object according to claim 7, wherein an inner transmittance is 80% or greater over a wavelength range from 400 nm to 450 nm.

12. An optical element using the cured object according to claim 7.

13. An optical system comprising the optical element according to claim 12.

14. An interchangeable camera lens comprising the optical system according to claim 13.

15. An optical device comprising the optical system according to claim 13.

16. A cemented lens comprising a first lens element and a second lens element joined with each other through intermediation of the cured object according to claim 7.

17. An optical system comprising the cemented lens according to claim 16.

18. An interchangeable camera lens comprising the optical system according to claim 17.

19. An optical device comprising the optical system according to claim 17.

20. A method for manufacturing a cemented lens comprising:
- a contacting step of contacting a first lens element and a second lens element with each other through intermediation of the resin precursor according to claim 2; and
- a joining step of curing the resin precursor to join the first lens element and the second lens element with each other.

21. The method for manufacturing a cemented lens according to claim 20, wherein, in the joining step, the resin precursor is irradiated with light to be cured.

22. The method for manufacturing a cemented lens according to claim 21, wherein the light radiates to the resin precursor through the first lens element.

23. The method for manufacturing a cemented lens according to claim 21, wherein the light radiates to the resin precursor through the second lens element.

* * * * *

UNITED STATES PATENT AND TRADEMARK OFFICE
CERTIFICATE OF CORRECTION

PATENT NO. : 12,248,119 B2
APPLICATION NO. : 17/565881
DATED : March 11, 2025
INVENTOR(S) : Yoshihiro Someya et al.

Page 1 of 1

It is certified that error appears in the above-identified patent and that said Letters Patent is hereby corrected as shown below:

On the Title Page

Item (57), Abstract, Column 2, Line 2:
Delete "of a" and insert -- or a --.

In the Claims

Column 37, Line 66 In Claim 1:
Before "wherein" insert -- , --.

Column 38, Line 33 In Claim 4:
Before "wherein" insert -- , --.

Column 38, Line 41-42 In Claim 5:
Delete "9,9-bis [4-(2-acryloyloxyethoxy)phenyl]fluorene," and insert -- 9,9-bis[4-(2-acryloyloxyethoxy)phenyl]fluorene, --.

Column 38, Line 53 In Claim 10:
Delete "(vd)" and insert -- ($v_d$) --.

Signed and Sealed this
Third Day of June, 2025

Coke Morgan Stewart
*Acting Director of the United States Patent and Trademark Office*